United States Patent
Chen et al.

(10) Patent No.: US 12,092,633 B2
(45) Date of Patent: Sep. 17, 2024

(54) BLOOD DETECTION METHOD AND BLOOD ANALYSIS SYSTEM

(71) Applicant: Shenzhen Mindray Bio-Medical Electronics Co., Ltd., Shenzhen (CN)

(72) Inventors: Gengwen Chen, Shenzhen (CN); Ziqian Zhang, Shenzhen (CN); Yi Ye, Shenzhen (CN); Zhaoyang Li, Shenzhen (CN)

(73) Assignee: Shenzhen Mindray Bio-Medical Electronics Co., Ltd., Shenzhen (CN)

(*) Notice: Subject to any disclaimer, the term of this patent is extended or adjusted under 35 U.S.C. 154(b) by 953 days.

(21) Appl. No.: 17/081,195

(22) Filed: Oct. 27, 2020

(65) Prior Publication Data
US 2021/0102935 A1   Apr. 8, 2021

Related U.S. Application Data

(63) Continuation of application No. PCT/CN2019/084660, filed on Apr. 26, 2019.

(30) Foreign Application Priority Data

Apr. 28, 2018 (CN) .......................... 201810402676.1

(51) Int. Cl.
*G01N 1/00* (2006.01)
*G01N 15/1429* (2024.01)
(Continued)

(52) U.S. Cl.
CPC ..... *G01N 33/5094* (2013.01); *G01N 15/1429* (2013.01); *G01N 33/49* (2013.01)

(58) Field of Classification Search
None
See application file for complete search history.

(56) References Cited

U.S. PATENT DOCUMENTS

| | | |
|---|---|---|
| 4,099,917 A | 7/1978 | Kim |
| 4,336,029 A | 6/1982 | Natale |
| (Continued) | | |

FOREIGN PATENT DOCUMENTS

| | | |
|---|---|---|
| CN | 101490547 A | 7/2009 |
| CN | 101726461 A | 6/2010 |
| (Continued) | | |

OTHER PUBLICATIONS

Wenger-Riggenbach, B. et al., "Evaluation of the Laser Cyte: an in-house hematology analyzer for dogs and cats," Comparative Clinical Pathology, vol. 15, No. 2, Jun. 2006, pp. 117-129, XP019461479, 13 pages.

*Primary Examiner* — Jyoti Nagpaul
(74) *Attorney, Agent, or Firm* — Kory D. Christensen

(57) ABSTRACT

A blood detection method is provided, including: treating a blood sample with a first reagent to obtain a test sample, wherein the first reagent includes a hemolytic agent for lysing red blood cells in the blood sample into fragments having light scattering characteristics significantly different from those of platelets; passing particles in the test sample through a detection area of an optical detection system one by one, to obtain optical information of the test sample; and obtaining optical information of platelets according to at least two types of the optical information of the test sample. In the method, a platelet count is obtained by lysing red blood cells in a blood sample, and white blood cell sub-populations can be also differentiated.

17 Claims, 13 Drawing Sheets

(51) Int. Cl.
    *G01N 33/49*         (2006.01)
    *G01N 33/50*         (2006.01)

(56) References Cited

U.S. PATENT DOCUMENTS

| | | |
|---|---|---|
| 5,817,519 A | 10/1998 | Zelmanovic et al. |
| 2005/0002826 A1 | 1/2005 | Oguni et al. |
| 2007/0105231 A1 | 5/2007 | Riley et al. |
| 2009/0153836 A1 | 6/2009 | Lindberg |
| 2011/0027788 A1 | 2/2011 | Zhao et al. |
| 2014/0185031 A1 | 7/2014 | Zhang et al. |
| 2018/0233366 A1* | 8/2018 | Nouri .................. H01L 21/3086 |

FOREIGN PATENT DOCUMENTS

| | | |
|---|---|---|
| CN | 101988082 A | 3/2011 |
| CN | 102155927 A | 8/2011 |
| CN | 102230994 A | 11/2011 |
| CN | 102243339 A | 11/2011 |
| CN | 104321635 A | 1/2015 |
| CN | 104749144 A | 7/2015 |
| CN | 106525666 A | 3/2017 |
| CN | 107525758 A | 12/2017 |
| EP | 0 774 113 B1 | 9/2005 |
| WO | WO 9604544 A1 | 2/1996 |

\* cited by examiner

A

B

A

B

BLOOD DETECTION METHOD AND BLOOD ANALYSIS SYSTEM

CROSS-REFERENCE

This application is a continuation of International Application No. PCT/CN2019/084660, filed Apr. 26, 2019, which claims priority benefit of Chinese patent application No. 201810402676.1, filed Apr. 28, 2018, the contents of which are incorporated herein by reference.

TECHNICAL FIELD

The present disclosure relates to blood detection and, in particular, to an optical detection method for platelets and a blood analysis system thereof.

BACKGROUND ART

Human blood contains various types of cells, such as red blood cells, white blood cells, platelets, etc. Platelets are non-nucleated cells with a diameter of 2-3 microns, and normal human blood contains 150,000 to 350,000 platelets per microliter.

The electrical impedance method is one of the commonly used measurement methods for platelets. This method is as follows: a sample containing blood cells is passed through an aperture with two electrodes; the impedance changes as a blood cell (such as a platelet) passes through, thus an impedance pulse is generated; and then the detected pulses are drawn as a histogram for analysis. In normal blood, the volume of a platelet is the smallest, the volume of a white blood cell is the largest, and the volume of a red blood cell is intermediate. The detected pulse intensity is related to the volume of the cell passing through the aperture, therefore different types of cells can be differentiated by volume division. However, when some special samples (such as samples containing platelets relatively large in volume and red blood cells relatively small in volume) are tested using this method, the detection accuracy and precision of platelets will be affected. These special samples usually come from subjects with diseases, so the deviation of detection values will have adverse effects on clinical diagnosis.

For this situation, a method for labeling and counting platelets by using a labeled antibody specific to surface antigens of platelets has been developed, see, e.g., American Journal of Clinical Pathology (2001): 115, p460-464. This method requires an antigen-antibody reaction during the test, so it takes a long time to obtain results. Therefore, this method is not suitable for measurements that are required for urgent judgments, such as whether blood transfusion is required or not, etc. Moreover, detection reagents used in this method are also relatively expensive.

Flow cytometry can be used for quickly measuring cells in blood. For example, U.S. Pat. Nos. 6,114,173, 4,882,284 and 5,891,731 all have disclosed a method for better differentiate platelets by staining blood cells with a dye under a non-hemolysis condition. However, sometimes broken red blood cells, lipids and the like may appear in blood, their sizes are similar to that of platelets, and they are stained as well, thus becoming impurities that affect the measurement of platelets. Especially when measuring a sample having a low platelet count and requiring blood transfusion, the influences of these impurities will be greater.

For this situation, a specific dye is disclosed in SYSMEX Inc.'s Chinese Patent Application Publication CN 101173921, which is capable of effectively differentiating platelets from impurities such as other blood cells, lipid particles and the like in the direction of fluorescence. However, this method needs to be implemented in a separate test channel, and this dye is still incapable of effectively differentiating red blood cell fragments from platelets.

Therefore, there is still a need to further improve the measurement methods for platelets.

SUMMARY OF THE DISCLOSURE

In view of the above situations, an object of the present disclosure is to provide a novel blood detection method, which is capable of accurately detecting platelets in a blood sample according to optical information by utilizing a hemolyzed sample.

A further object of the present disclosure is to further detect white blood cells in blood and further give an alarm for reticulocytes or detect reticulocytes according to optical information in the above-mentioned detection method.

Another object of the present disclosure is to provide a blood detection system for implementing the above-mentioned method.

To achieve the above-mentioned objects, the present disclosure firstly provides a first blood detection method, the method comprising: treating a blood sample with a first reagent to obtain a test sample, wherein the first reagent comprises a hemolytic agent for lysing red blood cells in the blood sample into fragments having light scattering characteristics significantly different from those of platelets; passing particles in the test sample through a detection area of an optical detection system one by one to obtain optical information of the test sample; and obtaining optical information of platelets according to at least two types of the optical information of the test sample.

According to an embodiment, the at least two types of the optical information of the test sample are forward scattered light intensity and side scattered light intensity so as to differentiate platelets and lysed red blood cell fragments.

In this embodiment, the method further comprises obtaining optical information of white blood cells according to the optical information of the forward scattered light intensity and the side scattered light intensity, preferably differentiating white blood cell subpopulations according to the obtained optical information of the white blood cells to obtain the white blood cell subpopulations which at least comprise monocytes, lymphocytes and neutrophils.

Specifically, the hemolytic agent comprises at least one selected from alkyl glycoside, triterpenoid saponin, and steroidal saponin.

According to one embodiment, the alkyl glycoside is selected from glycoside compounds having the general formula I:

$$R-(CH_2)_n-CH_3 \qquad (I)$$

wherein R is selected from the group consisting of monosaccharide, deoxy monosaccharide and polysaccharide, and n is an integer of 5-17.

The monosaccharide may be selected from pentose, methyl pentose and hexose, wherein the pentose comprises such as arabinose, xylose, ribose, lyxose, etc.; the methyl pentose comprises such as fusose, rhamnose, quinovose, etc.; the hexose comprises such as glucose, mannose, fructose, galactose and sorbose; the deoxy monosaccharide comprises such as deoxyribose, deoxyglucose, etc.; and the polysaccharide comprises such as maltose, sucrose, etc.

n is preferably an integer of 6 to 14, more preferably an integer of 7 to 11.

Further preferably, the first reagent further comprises:
a nonionic surfactant having the general formula II:

wherein $R_1$ is a C8-C23 alkyl group, $R_2$ is —O—,

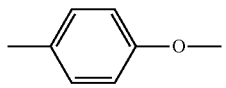

or —COO—, and m is an integer of 10 to 50; and
optionally, at least one organic acid or a salt thereof, wherein the organic acid or the salt thereof is selected from the group consisting of organic acids having at least one carboxyl group or sulfonic acid group and alkali metal salts thereof.

In the nonionic surfactant having the general formula II, preferably, R1 is a C8-C18 linear alkyl group. The C8-C18 linear alkyl group may specifically be octyl, decyl, lauryl, tetradecyl, hexadecyl or stearyl. More preferably, R1 is a C12-C16 linear alkyl group, which may specifically be lauryl, tetradecyl, or hexadecyl. R2 is preferably —O—. m is preferably 15 to 30.

In this embodiment, the first reagent preferably contains 0.025 g/L to 10 g/L, preferably 0.1 g/L to 5.0 g/L glycoside compound having the general formula I, and 0.03 g/L to 1.5 g/L, preferably 0.05 g/L~1.0 g/L non-ionic surfactant having the general formula II.

The first agent may further comprise one or more selected from a buffer agent, a metal chelating agent, an osmotic pressure regulator and a preservative.

In a specific embodiment, the volume mixing ratio of the blood sample to the first reagent may be 1:4~1:60. The blood sample is treated with the first reagent at a temperature such as 40° C. to 60° C. and the two react with each other for 15-100 seconds, preferably for 40-80 seconds.

According to this embodiment, red blood cells in the test sample are deeply lysed after being treated with the first reagent, but cell morphology of platelets still maintain unchanged so that the scattered light properties of the obtained red blood cell fragments and the scattered light properties of platelets are significantly different. The optical information of platelets can be accurately obtained based on a scatter diagram obtained according to intensities of forward scattered light and side scattered light, thereby realizing accurate counting of platelets under a hemolysis condition.

According to another embodiment, the method further comprises treating the blood sample with a second reagent which comprises a fluorescent dye.

In this embodiment, passing particles in the test sample through the detection area of the optical detection system one by one, and obtaining optical information of the test sample further comprises obtaining fluorescence information, and white blood cell subpopulations are differentiated to obtain the white blood cell subpopulations which at least comprise monocytes, lymphocytes and neutrophils, and/or immature granulocytes are identified according to side scattered light intensity information and fluorescence intensity information.

In this embodiment, according to an implementation, the fluorescence dye comprises a first fluorescence dye selected from a membrane-specific dye and a mitochondrion-specific dye.

Preferably, the membrane-specific dye is selected from the group consisting of DiA, DiD, DiI, DiO, DiR, DiS, FDA, Alexa Fluor 488, Super Fluor 488 and variant structures using them as parents, and the mitochondrion-specific dye is selected from the group consisting of Janus Green B, Mito-Lite Red, Rhodamine 123 and Mitotracker series as well as variant structures of their parents.

In one embodiment, the mitochondrion-specific dye is Rhodamine 123, Mitotracker Deep Red or Mitotracker Red.

In the present disclosure, the Mitotracker series dyes may comprise Mitotracker Green, Mitotracker Deep Red, and Mitotracker Red, etc.

In this implementation, platelets are identified according to fluorescence intensity information and forward scattered light intensity information.

Further, an alarm for reticulocytes is provided when a number of particles in a preset region of a scatter diagram generated according to forward scattered light intensity and fluorescence intensity exceeds a predetermined threshold value.

In this embodiment, according to another implementation, the fluorescence dye comprises a second fluorescence dye selected from nucleic acid-specific dyes. Preferably, the nucleic acid-specific dyes are nucleic acid-specific dyes for reticulocytes.

In this implementation, the method further comprises identifying reticulocytes according to fluorescence intensity information and scattered light intensity information.

Furthermore, the method further comprises counting reticulocytes according to fluorescence intensity information and forward scattered light intensity information.

In this embodiment, according to another implementation, the fluorescence dye comprises a first fluorescence dye selected from a membrane-specific dye and a mitochondrion-specific dye and a second fluorescence dye selected from nucleic acid-specific dyes.

In this implementation, the method further comprises differentiating platelets and reticulocytes according to fluorescence intensity information and side scattered light intensity information.

The aforementioned blood detection methods of the present disclosure can all be used for counting platelets according to the obtained optical information of platelets.

According to another embodiment of the present disclosure, the methods of the present disclosure can further be implemented in an optical detection system capable of eliminating interference of reflected light to a laser, wherein the optical detection system comprises an optical subsystem, a flow chamber and first detector.

The optical subsystem comprises a laser, a front optical assembly and a rear optical assembly, and the front optical assembly comprises an optical isolator, wherein the laser is configured to emit a laser beam; the front optical assembly is configured to perform front optical treatment on the laser beam, so that the laser beam subjected to the front optical treatment is converged in a first direction at the blood cell sample to be tested in the flow chamber, and scattered light is generated; the rear optical assembly is disposed downstream of the flow chamber along the propagation direction of the laser beam, and is configured to perform rear optical treatment on the scattered light, so that the scattered light subjected to the rear optical treatment enters the first detector for light intensity detection; the optical isolator is configured to isolate reflected light from the laser, wherein the reflected light is generated when the laser beam passes through the flow chamber.

According to a specific embodiment, the optical isolator comprises a beam splitter prism and a polarization conversion element which are adhesively connected with each other; the beam splitter prism is configured to reflect the S-polarization component of the incident laser beam and transmit the P-polarization component of the incident laser beam; the polarization conversion element is configured to change the polarization state of the P-polarization component transmitted through the beam splitter prism, so that the P-polarization component is changed from linearly polarized light into circularly polarized light, and to change the polarization state of the circularly polarized light after reflection into S-polarized light so that the S-polarized light is reflected by the beam splitter prism.

According to another specific embodiment, the optical isolator comprises a polarization analyzer and a polarization conversion element which are adhesively connected with each other; the polarization analyzer is configured to allow only the P-polarization component of the laser beam to pass through; the polarization conversion element is configured to change the polarization state of the P-polarization component passing through the polarization analyzer, so that the P-polarization component is changed from linearly polarized light into circularly polarized light, and to change the polarization state of reflected light of the circularly polarized light into S-polarized light so that the S-polarized light is isolated by the polarization analyzer.

In an embodiment, the front optical assembly further comprises a collimating lens, wherein the collimating lens is disposed between the laser and the optical isolator along the propagation direction of the laser beam, and is configured to collimate the laser beam to make the laser beam become a parallel beam.

In an embodiment, the rear optical assembly further comprises a blocking diaphragm, and the front optical assembly is further configured to perform front optical treatment on the laser beam so that the laser beam subjected to the front optical treatment is converged at the blocking diaphragm in a second direction.

In an embodiment, the front optical assembly further comprises a first light converging element and a second light converging element, wherein the first light converging element is configured to perform first focusing on the laser beam so that the laser beam is converged in the first direction at the blood cell sample to be tested in the flow chamber, and scattered light is generated, and the second light converging element is configured to perform second focusing on the laser beam so that the laser beam is converged at the blocking diaphragm included by the rear optical assembly in a second direction.

In an embodiment, the rear light assembly further comprises a third converging element and an aperture diaphragm, wherein the third light converging element is configured to perform third focusing on the scattered light so that the scattered light is converged at the aperture diaphragm and enters the first detector via the aperture of the aperture diaphragm.

In the above-mentioned implementations, the optical detection system further comprises a second detector and a fluorescence detector; the second detector is configured to detect the intensity of scattered light which forms an angle within a preset angle range (for example, 60° to 120°) with the propagation direction of the laser beam; and the fluorescence detector is configured to detect fluorescence generated by the blood cell sample to be tested.

In the above-mentioned implementations, the second direction is perpendicular to the flow direction of the blood cell sample to be tested; and the first direction is the same as the flow direction of the blood cell sample to be tested.

In the above-mentioned implementations, the optical isolator has an optical isolation degree not smaller than 30 db.

In the above-mentioned implementations, the blocking diaphragm has a light collection angle of 1-10°.

In the above-mentioned implementations, the laser beam has a wavelength of 630 nm to 640 nm.

In the above-mentioned implementations, the laser beam is P-linearly polarized light. Reflected light generated when a laser beam is propagated in an optical path can be commendably isolated by the above-mentioned optical detection system, so that the laser can stably output a laser beam, thereby avoiding small pulses occurring due to power peaks generated when the reflected light enters the laser, also avoiding confusion between those interfering small pulses and small pulses generated by platelet particles, and further improving the detection precision of platelets using the methods disclosed by the present disclosure.

The present disclosure hereby further provides a second blood detection method, and the method comprises: treating a blood sample with a first reagent to obtain a test sample, wherein the first reagent comprises a hemolytic agent for lysing red blood cells in the blood sample; passing particles in the test sample through a detection area of an optical detection system one by one to obtain optical information of the test sample; and obtaining optical information of platelets according to at least two types of the optical information of the test sample.

According to a first embodiment, the hemolytic agent is used for lysing red blood cells in the blood sample into fragments having light scattering characteristics significantly different from those of platelets.

In the first embodiment, the first reagent comprises at least one hemolytic agent selected from alkyl glycoside, triterpenoid saponin and steroidal saponin.

According to the first embodiment, the alkyl glycoside is selected from glycoside compounds having the general formula I:

$$R-(CH_2)_n-CH_3 \quad (I)$$

wherein R is selected from the group consisting of monosaccharide, deoxy monosaccharide and polysaccharide, and n is an integer of 5-17.

The monosaccharide may be selected from pentose, methyl pentose and hexose, wherein the pentose comprises such as arabinose, xylose, ribose, lyxose, etc.; the methyl pentose comprises such as fusose, rhamnose, quinovose, etc.; the hexose comprises such as glucose, mannose, fructose, galactose and sorbose; the deoxy monosaccharide comprises such as deoxyribose, deoxyglucose, etc.; and the polysaccharide comprises such as maltose, sucrose, etc.

n is preferably an integer of 6 to 14, more preferably an integer of 7 to 11.

According to one embodiment, the first reagent further comprises a nonionic surfactant having the general formula II:

$$R_1-R_2-(CH_2CH_2)_m-H \quad (II)$$

wherein $R_1$ is a C8-C23 alkyl group, $R_2$ is —O—,

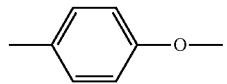

or —COO—, and m is an integer of 10 to 50; and
optionally, at least one organic acid or a salt thereof, wherein the organic acid or the salt thereof is selected from the group consisting of organic acids having at least one carboxyl group or sulfonic acid group and alkali metal salts thereof.

In the nonionic surfactant having the general formula II, preferably, R1 is a C8-C18 linear alkyl group. The C8-C18 linear alkyl group may specifically be octyl, decyl, lauryl, tetradecyl, hexadecyl or stearyl. More preferably, R1 is a C12-C16 linear alkyl group, which may specifically be lauryl, tetradecyl, or hexadecyl. R2 is preferably —O—. m is preferably 15 to 30.

In this embodiment, the first reagent preferably contains 0.025 g/L to 10 g/L, preferably 0.1 g/L to 5.0 g/L glycoside compound having the general formula I, and 0.03 g/L to 1.5 g/L, preferably 0.05 g/L~1.0 g/L non-ionic surfactant having the general formula II.

The first agent may further comprise one or more selected from a buffer agent, a metal chelating agent, an osmotic pressure regulator and a preservative.

In a specific embodiment, the volume mixing ratio of the blood sample to the first reagent may be 1:4~1:60. The blood sample is treated with the first reagent at a temperature such as 40° C. to 60° C. and the two react with each other for 15-100 seconds, preferably for 40-80 seconds.

According to the blood detection method provided by the first embodiment, wherein the at least two types of the optical information of the test sample are forward scattered light intensity and side scattered light intensity.

According to this embodiment, red blood cells in the test sample are deeply lysed after being treated with the first reagent, but cell morphology of platelets still maintain unchanged so that the scattered light properties of the obtained red blood cell fragments and the scattered light properties of platelets are significantly different. The optical information of platelets can be accurately obtained based on a scatter diagram obtained according to intensities of forward scattered light and side scattered light, thereby realizing accurate counting of platelets under a hemolysis condition.

In this embodiment, according to one implementation, the method further comprises further treating the blood sample with a second reagent after treating the blood sample with the first reagent so as to obtain a test sample.

The second reagent comprises a dye selected from a membrane-specific dye and a mitochondrion-specific dye.

In one embodiment, the membrane-specific dye is selected from DiA, DiD, DiI, DiO, DiR, DiS, FDA, Alexa Fluor 488 and Super Fluor 488.

According to one embodiment, the mitochondrion-specific dye is selected from Janus Green B, MitoLite Red, Rhodamine 123 and Mitotracker series.

In one embodiment, the mitochondrion-specific dye is Rhodamine 123, Mitotracker Deep Red or Mitotracker Red.

In the present disclosure, the Mitotracker series of dyes may comprise Mitotracker Green, Mitotracker Deep Red, Mitotracker Red, etc.

In some embodiments, the second reagent of the present disclosure further comprises variant structures, parents of which are the above-mentioned dyes.

After the blood sample is treated with the first reagent containing a hemolytic agent and the second reagent containing a membrane-specific dye or a mitochondrion-specific dye, the fluorescence characteristics of platelets and lysed red blood cells become more significantly different, so that platelets can be further differentiated from lysed red blood cell fragments by detecting the fluorescence intensity and at least one of the forward scattered light intensity and the side scattered light intensity, especially by detecting the fluorescence intensity and the forward scattered light intensity.

Therefore, in this implementation, platelets may be identified according to the fluorescence intensity information and the side scattered light intensity information; white blood cell subpopulations may be differentiated to obtain the white blood cell subpopulations at least including monocytes, lymphocytes and neutrophils and/or immature granulocytes may be identified according to the side scattered light intensity information and the fluorescent intensity information; and/or an alarm for reticulocytes may be provided when a number of particles in a preset region of a scatter diagram generated by the forward scattered light intensity and the fluorescence intensity exceeds a predetermined threshold value.

In this embodiment, according to another implementation, the second reagent comprises a nucleic acid-specific dye, or comprises both a dye selected from a membrane-specific dye and a mitochondrion-specific dye and a nucleic acid-specific dye. In this implementation, the organelles released after red blood cells are lysed, by being stained with the nucleic acid-specific dye, can be used to further differentiate nucleated reticulocyte fragments from platelets, and accurate optical information of reticulocytes can also be obtained, thereby simultaneously obtaining the optical information of platelets, white blood cells, and reticulocytes in one optical detection by utilizing the method of the first embodiment.

Therefore, according to one implementation, the blood detection method further comprises differentiating platelets and reticulocytes according to the fluorescence intensity information and the scattered light intensity information. And more preferably, according to the fluorescence intensity information and the forward scattered light intensity information, platelets are differentiated from reticulocytes, and reticulocytes may be counted. All contents of the first embodiment of the second blood detection method are also applicable to the first blood detection method of the present disclosure. And all contents in the first blood detection method are also applicable to the first embodiment of the second blood detection method.

According to a second embodiment of the present disclosure, the blood detection method comprises: treating the blood sample with a first reagent and a second reagent to obtain a test sample, wherein the first reagent comprises a hemolytic agent.

According to the second embodiment, the hemolytic agent is not particularly limited, and conventional hemolytic agents for red blood cells in the art may be applied to this embodiment.

The second reagent used in this embodiment is the same as that used in the first embodiment and may comprise a dye selected from the above-mentioned membrane-specific dyes and the above-mentioned mitochondrion-specific dyes.

Also, after the blood sample is treated with the first reagent containing a hemolytic agent and the second reagent containing a membrane-specific dye or a mitochondrion-specific dye, the fluorescence characteristics of platelets and lysed red blood cells become more significantly different, so that platelets can be further differentiated from the lysed red blood cell fragments by detecting the fluorescence intensity and at least one of the forward scattered light intensity and the side scattered light intensity, especially by detecting the fluorescence intensity and the forward scattered light intensity. Due to the use of the membrane-specific dye or the mitochondrion-specific dye, in this embodiment, red blood cells lysed only by a conventional hemolytic agent can be clearly differentiated from platelets based on a two-dimensional scatter diagram, without deeply lysing red blood cells as in the first embodiment.

In this embodiment, according to fluorescent intensity information and side scattered light intensity information, white blood cell subpopulations may be differentiated to obtain the white blood cell subpopulations at least including monocytes, lymphocytes and neutrophils, and/or immature granulocytes may be identified; platelets are fully differentiated according to fluorescent intensity information and forward scattered light intensity information; and/or an alarm for reticulocytes is provided when a number of particles in a preset region of a scatter diagram generated according to the forward scattered light intensity and the fluorescence intensity exceeds a predetermined threshold value.

Also, in this embodiment, the second reagent may further comprise a fluorescence dye selected from nucleic acid-specific dyes. In this way, platelets may be further differentiated from reticulocytes, and preferably reticulocytes are further counted, according to fluorescence intensity information and forward scattered light intensity information.

According to a third embodiment, the above-mentioned blood detection method provided by the present disclosure may obtain the optical information through detection by an optical detection system, and the optical detection system comprises:
  an optical subsystem, a flow chamber and a first detector;
  the optical subsystem comprises a laser, a front optical assembly comprising an optical isolator, and a rear optical assembly comprising a blocking diaphragm, wherein
  the laser is configured to emit a laser beam;
  the front optical assembly is configured to perform front optical treatment on the laser beam, so that the laser beam subjected to the front optical treatment is converged at the blocking diaphragm in a second direction and converged in a first direction at the blood cell sample to be tested in the flow chamber, and scattered light is generated;
  the rear optical assembly is disposed downstream of the flow chamber along the propagation direction of the laser beam, and is configured to perform rear optical treatment on the scattered light and the laser beam converged at the blocking diaphragm, so that the scattered light subjected to the rear optical treatment enters the first detector for light intensity detection;
  the optical isolator is configured to isolate reflected light from the laser, wherein the reflected light is generated when the laser beam passes through the flow chamber and the rear optical assembly.

In the above-mentioned implementations, the optical isolator comprises a beam splitter prism and a polarization conversion element which are adhesively connected with each other;
  the beam splitter prism is configured to reflect the S-polarization component of the incident laser beam and transmit the P-polarization component of the incident laser beam;
  the polarization conversion element is configured to change the polarization state of the P-polarization component transmitted through the beam splitter prism, so that the P-polarization component is changed from linearly polarized light into circularly polarized light, and to change the polarization state of the circularly polarized light after reflection into S-polarized light so that the S-polarized light is reflected by the beam splitter prism.

In the above-mentioned implementations, the optical isolator comprises a polarization analyzer and a polarization conversion element which are adhesively connected with each other;
  the polarization analyzer is configured to allow only the P-polarization component of the laser beam to pass through;
  the polarization conversion element is configured to change the polarization state of the P-polarization component passing through the polarization analyzer, so that the P-polarization component is changed from linearly polarized light into circularly polarized light, and to change the polarization state of reflected light of the circularly polarized light into S-polarized light so that the S-polarized light is isolated by the polarization analyzer.

In the above-mentioned implementations, when the laser beam is incident to the optical isolator perpendicularly, the reflectivity of the first incident surface of the beam splitter prism is not greater than 0.5%.

In the above-mentioned implementations, the optical isolator comprises a bandpass filter and a frequency-doubling crystal which are adhesively connected with each other;
  the bandpass filter is configured to allow the laser beam with a wavelength $\lambda$ to pass through;
  the frequency-doubling crystal is configured to perform frequency doubling on the laser beam passing through the bandpass filter and perform frequency doubling again on reflected light of the frequency-doubled laser beam, so that the reflected light is filtered out by the bandpass filter.

In the above-mentioned implementations, the front optical assembly further comprises a collimating lens;
  the collimating lens is disposed between the laser and the optical isolator along the propagation direction of the laser beam and is configured to collimate the laser beam to make the laser beam become a parallel beam.

In the above-mentioned implementations, the front optical assembly further comprises a first light converging element and a second light converging element;
  the first light converging element is configured to perform first focusing on the laser beam, so that the laser beam is converged in the first direction at the blood cell sample to be tested in the flow chamber, and scattered light is generated;
  the second light converging element is configured to perform second focusing on the laser beam so that the laser beam is converged at the blocking diaphragm.

In the above-mentioned implementations, the rear optical assembly further comprises a third converging element and an aperture diaphragm;
  the third converging element is configured to perform third focusing on the scattered light so that the scattered light is converged at the aperture diaphragm and enters the first detector via the aperture of the aperture diaphragm.

In the above-mentioned implementations, the optical detection system further comprises a second detector and a fluorescence detector;
  the second detector is configured to detect the intensity of scattered light which forms an angle within a preset angle range (for example, 60° to 120°) with the propagation direction of the laser beam;

and the fluorescence detector is configured to detect fluorescence generated by the blood cell sample to be tested.

In the above-mentioned implementations, the second direction is perpendicular to the flow direction of the blood cell sample to be tested;

and the first direction is the same as the flow direction of the blood cell sample to be tested.

In the above-mentioned implementations, the optical isolator has an optical isolation degree not smaller than 30 db.

In the above-mentioned implementations, the blocking diaphragm has a light collection angle of 1-10°.

In the above-mentioned implementations, the laser beam has a wavelength of 630 nm to 640 nm.

In the above-mentioned implementations, the laser beam is P-linearly polarized light. Reflected light generated when a laser beam is propagated in an optical path can be commendably isolated by the above-mentioned optical detection system, so that the laser can stably output a laser beam, thereby avoiding small pulses occurring due to power peaks generated when the reflected light enters the laser, also avoiding confusion between those interfering small pulses and small pulses generated by platelet particles, and further improving the detection precision of platelets using the methods disclosed by the present disclosure.

According to an object of another aspect of the present disclosure, the present disclosure also provides a blood analysis system comprising:

a sampling part configured to obtain a blood sample and convey the blood sample to a reaction part;

a reagent supply part configured to store at least a first reagent and supply the first reagent to the reaction part as required;

the reaction part comprising a mixing chamber, wherein the mixing chamber is configured to mix the blood sample with the first reagent to prepare a test sample, wherein the first reagent comprises a hemolytic agent for lysing red blood cells in the blood sample;

an optical detection system comprising a flow chamber and at least a first detector, wherein the optical detection system is configured to detect particles in the test sample by the first detector when the test sample is conveyed from the mixing chamber to the optical detection system and particles in the test sample are made to pass through the flow chamber one by one to reach a detection area, so as to obtain optical information of the test sample; and a data processing part operatively connected with the optical detection system and comprising a processor and a non-transitory computer-readable storage medium storing a computer program, wherein when the computer program is executed by the processor, the following step is performed: obtaining optical information of platelets according to at least two types of the optical information of the test sample.

According to a first embodiment of the blood analysis system provided by the present disclosure, the hemolytic agent is used for lysing red blood cells in the blood sample into fragments having light scattering characteristics significantly different from those of platelets; and in the processing module, when the computer program is executed by the processor, the following steps are further performed:

counting platelets according to forward scattered light intensity and side scattered light intensity of the obtained optical information; and/or differentiating white blood cells at least into monocyte subpopulation, lymphocyte subpopulation and neutrophil subpopulation according to the forward scattered light intensity and the side scattered light intensity.

According to a second embodiment of the blood analysis system provided by the present disclosure, wherein the mixing chamber is configured to mix the blood sample with a second reagent to prepare a test sample, wherein the second reagent comprises a fluorescence dye selected from a membrane-specific dye and a mitochondrion-specific dye;

the optical detection system comprises a second detector, and the second detector is a fluorescence detector for further obtaining fluorescence signals when the particles in the test sample pass through the detection area one by one; and in the data processing part, when the computer program is executed by the processor, the following steps are further performed:

differentiating white blood cell subpopulations to obtain the white blood cell subpopulations at least including monocytes, lymphocytes and neutrophils, and/or identifying immature granulocytes, according to fluorescence intensity information and side scattered light intensity information;

fully differentiating platelets according to fluorescence intensity information and forward scattered light intensity information; and/or providing an alarm for reticulocytes when a number of particles in a preset region of a scatter diagram generated according to forward scattered light intensity information and fluorescence intensity information exceeds a predetermined threshold value.

In the second embodiment, according to another implementation, the second reagent further comprises a fluorescence dye selected from nucleic acid-specific dyes; and when the computer program is executed by the processor, the following steps are further performed: differentiating platelets and reticulocytes, preferably further counting reticulocytes, according to the fluorescence intensity information and the scattered light intensity information.

According to a third embodiment of the blood analysis system provided by the present disclosure, wherein the optical detection system further comprises an optical subsystem;

the optical subsystem comprises a laser, a front optical assembly and a rear optical assembly; and the front optical assembly comprises an optical isolator, wherein the laser is configured to emit a laser beam;

the front optical assembly is configured to perform front optical treatment on the laser beam, so that the laser beam subjected to the front optical treatment is converged in a first direction at the blood cell sample to be tested in the flow chamber, and scattered light is generated;

the rear optical assembly is disposed downstream of the flow chamber along the propagation direction of the laser beam, and is configured to perform rear optical treatment on the scattered light, so that the scattered light subjected to the rear optical treatment enters the first detector for light intensity detection;

the optical isolator is configured to isolate reflected light from the laser, wherein the reflected light is at least generated when the laser beam passes through the flow chamber.

It should be understood that, all the features of the aforementioned optical detection system of the present disclosure may be applied to the optical detection system of the blood analysis system of the present disclosure.

The present disclosure provides a brand-new blood detection method. In the method, a blood sample is hemolyzed and platelets in the blood sample can be accurately detected by optical detection, and an analysis result of white blood cells can be simultaneously obtained, and detection information of reticulocytes can be further obtained detection by using a nucleic acid-specific dye. Thus, differentiation of platelets under a hemolysis condition by utilizing optical information is realized for the first time, and detection information of white blood cells and even of reticulocytes can be obtained in a common channel simultaneously, so that the blood detection is simplified, and the detection cost is lowered.

DETAILED DESCRIPTION OF EMBODIMENTS

Figure 1:
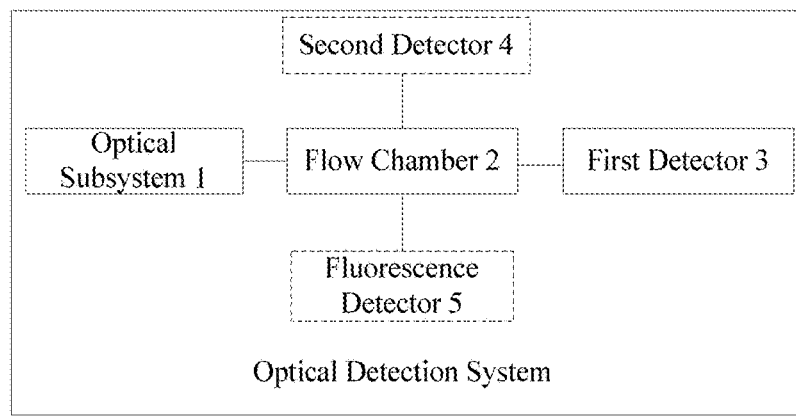
FIG. 1 illustrates a schematic structure diagram I of an optical detection system provided by an embodiment of the present disclosure.

The technical solutions in the embodiments of the present disclosure will be described clearly and fully in combination with the accompanying drawings in the embodiments of the present disclosure. Obviously, the described embodiments are only some embodiments of the present disclosure, but not all embodiments. Based on the embodiments in the present disclosure, all other embodiments obtained by those of ordinary skill in the art without any creative efforts shall fall within the protection scope of the present disclosure.

Throughout the specification, unless otherwise specifically stated, the terms used herein should be understood to have the meaning commonly used in the art. Therefore, unless otherwise defined, all technical and scientific terms used herein have the same meaning as commonly understood by those of ordinary skill in the art to which the present disclosure belongs. If there are conflicts, this specification takes precedence.

It should be noted that, in the embodiments of the present disclosure, the term "comprise", "include", or any other variant is intended to cover a non-exclusive meaning, so that a method or a device comprising a set of elements not only comprises expressly recorded elements but also comprises other elements not expressly listed, or further comprises inherent elements for implementing the method or the device. Without further limits, an element defined by the sentence "comprising a . . . " does not exclude that other relevant elements (for example, steps in a method or units in a device, herein the units may be some circuits, some processors, some programs, or software, etc.) are further comprised in the method or device comprising the element.

It should be noted that, the terms "first/second/third" related to the embodiments of the present disclosure are only used to distinguish similar objects rather than representing specific sequence of the aimed objects, and it can be understood that "first/second/third" are interchangeable in a specific sequence or a precedence order under allowable conditions. It should be understood that the objects distinguished by "first/second/third" are interchangeable under proper conditions so that the examples of the present disclosure described herein can be implemented in a sequence in addition to those shown in the drawings or described herein.

As previously mentioned, in detection of platelets, it is conventional to adopt an electrical impedance method, but platelets cannot be detected accurately when the electrical impedance method is used to detect some special blood samples. Therefore, platelets are detected in a separate detection channel using an optical detection method combined with a specific detection reagent. These methods are all performed in a separate detection channel without hemolysis.

Generally, a red blood cell hemolytic agent may also damage other cell membranes while destroying red blood cell membranes. Also, a large amount of red blood cell fragments generated after hemolysis are usually considered to cause greater interference to the detection of platelets. Therefore, most currently known optical methods for detecting platelets are performed without hemolysis.

U.S. Pat. No. 7,344,890 B2 has disclosed a ghosting reagent for treating a blood sample containing interferents, so that the scattering characteristics of red blood cells are changed, thus the intensity and time-of-flight of the forward scattered light of the cells in the sample can be measured in order to clearly differentiate platelets from red blood cells on the obtained two-dimensional scatter diagram. In this method the refractive index of red blood cells is significantly changed by releasing hemoglobin from normal red blood cells. However, it cannot be effectively differentiated large-size platelets and white blood cells in this method. Moreover, in this method, it is required to measure time-of-flight, and platelets cannot be detected only by optical information.

The inventors have developed a method for detecting platelets by adopting an optical method with hemolysis treatment performed on a blood sample. In this method, platelets can be differentiated from red blood cells lysed by hemolysis treatment by utilizing optical information, and optical information of white blood cells can also be obtained at the same time, and optical information of reticulocytes can be further obtained by using a nucleic acid-specific dye.

The second blood detection method and the corresponding blood analysis system of the present disclosure are exemplarily described in detail below.

According to the blood detection method of the present disclosure, a blood sample is first treated with a first reagent including a hemolytic agent to obtain a test sample, then the test sample is detected by using an optical detection equipment, and platelets are differentiated from other particles in the test sample by utilizing at least two types of optical information, thereby obtaining optical information of platelets. It has been verified that the platelet count obtained by the method of the present disclosure is highly consistent with the results obtained by detection using other methods in the existing blood analyzers.

Furthermore, the method of the present disclosure does not affect the counting of white blood cells in a conventional white blood cell counting channel. In the obtained scatter diagram (further refer to the embodiments detailed below), the white blood cell region is significantly away from the platelet region. Therefore, in the method of the present disclosure, white blood cells would not interfere with large-size platelets and platelet aggregates. Thus, in the method of the present disclosure, a detection result of at least three classifications, even four classifications of white blood cells (with the use of a fluorescence dye) can obtained at the same time, and an alarm for reticulocytes can be given or reticulocytes can be counted.

The method of the present disclosure will be further described below through specific embodiments.

According to a first embodiment of the present disclosure, the first reagent comprises a hemolytic agent for deeply lysing red blood cells. The hemolytic agent is not particularly limited, and the red blood cell deep hemolytic agent of the present disclosure may be adopted. For example, such a hemolytic agent may be alkyl glycoside, triterpenoid saponin, steroidal saponin and the like.

A specific hemolytic agent may be a glycoside compound having the general formula I:

$$R\text{—}(CH_2)_n\text{—}CH_3 \tag{I}$$

wherein R is selected from the group consisting of monosaccharide, deoxy monosaccharide and polysaccharide, and n is an integer of 5-17.

The above glycoside compound is capable of quickly lysing red blood cells. The glycoside compound is a compound formed by dehydrating the hemiacetal hydroxyl of saccharide (or polysaccharide) and the hydroxyl of alkanol. The glycoside compound in the hemolytic agent of the disclosure may be a single compound or a mixture of two or more glycoside compounds in accordance with the above-mentioned general formula.

In the general formula (I), the monosaccharide is not particularly limited. The commonly used monosaccharide may be selected from pentose, methyl pentose and hexose, but is not limited thereto. The pentose comprises such as arabinose, xylose, ribose, lyxose, etc. The methyl pentose comprises such as fucose, rhamnose, quinovose, etc. The hexose comprises such as glucose, mannose, fructose, galactose and sorbose. The deoxy monosaccharide is also not particularly limited, and comprises such as deoxyribose, deoxyglucose, etc., but is not limited thereto. The polysaccharide comprises such as maltose, sucrose, etc., but is not limited thereto. n is preferably an integer of 6 to 14, more preferably an integer of 7 to 11.

The glycoside compound having the general formula I may specifically be octyl glucoside, nonyl glucoside, decyl glucoside, dodecyl maltoside, myristyl maltoside and dodecyl glucoside, preferably octyl glycoside, nonyl glucoside, decyl glucoside and dodecyl maltoside, more preferably decyl glucoside and dodecyl maltoside.

The concentration of the glycoside compound having the general formula I in the hemolytic agent of the present disclosure varies according to the properties of the selected glycoside, the reaction time, the reaction temperature and the dosage of other components. Generally, the dosage is within the range of 0.025 g/L to 10 g/L preferably within the range of 0.1 g/L to 5.0 g/L.

The first reagent in the first embodiment preferably further comprises:

a nonionic surfactant having the general formula II:

$$R_1\text{—}R_2\text{—}(CH_2CH_2O)_m\text{—}H \tag{II}$$

wherein $R_1$ is a C8-C23 alkyl group, R2 is —O—,

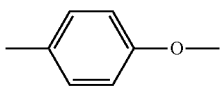

or —COO—, and m is an integer of 10 to 50; and
optionally, at least one organic acid or a salt thereof, wherein the organic acid or the salt thereof is selected from the group consisting of organic acids having at least one carboxyl group or sulfonic acid group and alkali metal salts thereof.

The nonionic surfactant having the general formula II is capable of binding to cell membranes to a certain extent, so as to achieve an effect of protecting the cell membranes of white blood cells and platelets from being influenced by the aforementioned glycoside compounds, thereby maintaining or substantially maintaining their cell morphologies.

According to some embodiments, in the nonionic surfactant having the general formula II, preferably, R1 is a C8-C18 linear alkyl group. The C8-C18 linear alkyl group may specifically be octyl, decyl, lauryl, tetradecyl, hexadecyl or stearyl. More preferably, R1 is a C12-C16 linear alkyl group, which may specifically be lauryl, tetradecyl, or hexadecyl. R2 is preferably —O—. m is an integer of 10 to 50, preferably 15 to 30.

Specific examples of the nonionic surfactant having the general formula II may be cetanol polyoxyethylene (15) ether, dodecanol polyoxyethylene (21) ether, cetanol polyoxyethylene (23) ether, cetanol polyoxyethylene (25) ether and cetanol polyoxyethylene (30) ether, but are not limited thereto.

The concentration of the nonionic surfactant having the general formula II is not particularly limited, but may be 0.03 g/L to 1.5 g/L, preferably 0.05 g/L to 1.0 g/L.

In the present disclosure, the nonionic surfactant may be used as a single substance or a mixture of two or more substances. Depending on the type of the nonionic surfactant used, the concentration thereof in the hemolytic agent varies. In general, the concentration of the nonionic surfactant with a longer alkyl chain and more repeat units in the polyoxyethylene part is relatively low.

In the present disclosure, the compounds having the general formula I and the general formula II are cooperatively used, so that on the one hand, the effect of quickly and deeply lysing red blood cells can be achieved, and on the other hand, cell membranes of platelets can be protected in order to effectively detect the platelets.

According to the selected compounds having the general formula I and the general formula II, their dosage ratio also varies. However, in general, the dosage ratio of the compounds having the general formula I and the general formula II is 1:100 to 1:3, preferably 1:25 to 1:5, and more preferably 1:10 to 1:5.

According to one embodiment of the present disclosure, the first reagent may further comprise at least one organic acid or a salt thereof to improve the differentiation degree of scattered light of white blood cells. The organic acid is preferably selected from the group consisting of C1-6 alkyl mono-, di-, or tri-carboxylic acid which is unsubstituted or substituted with a hydroxy group or an amino group, C1-6 alkyl sulfonic acid which is unsubstituted or substituted with a hydroxy group or an amino group, C6-10 aryl C1-6 alkyl acid, C6-10 aryl bi(C1-6 alkyl acid) and C6-10 aryl sulfonic acid.

Specific examples of the organic acid and its salt may be formic acid, acetic acid, benzoic acid, citric acid (3-hydroxy-1,3,5-pentyl triacid), malic acid (2-hydroxysuccinic acid), benzenedicarboxylic acid, benzenesulfonic acid, α-naphthalenesulfonic acid, taurine, etc. and their alkali metal salts such as sodium salts and potassium salts, but are not limited thereto.

The concentration of the organic acid or organic acid salt in the hemolytic agent is 0.05 g/L to 2 g/L, preferably 0.1 g/L to 0.5 g/L.

The first reagent of the present disclosure may further comprise conventional additives. These additives may be selectively added as needed, such as (but not limited to) a buffer agent, a metal chelating agent, an osmotic pressure regulator, a preservative, etc. These reagents are all commonly used reagents in the art, as long as they do not prevent the above components in the hemolytic agent of the present disclosure from functioning. The buffer agent may be, for example, one selected from phosphoric acid and its salts, citric acid and its salts, TRIS, etc., and is generally a buffer system composed of two or more of them. The metal chelating agent is used as an anticoagulant, for example, commonly used sodium EDTA. The osmotic pressure regulator is usually an inorganic salt such as sodium chloride, sodium sulfate, potassium sulfate, sodium borate, etc. The preservative is for example, isothiazolinone, sodium azide, and imidazolidinyl urea.

The mixing ratio of the first reagent according to the first embodiment to the blood sample is not particularly limited. For example, the volume mixing ratio of the blood sample to the first reagent may be 1:40 to 1:60. Hemolytic reaction is performed for 15-100 seconds, preferably for 40-80 seconds at a temperature such as 40 DEG C to 60 DEG C. The reaction temperature and the reaction time may be adjusted according to specific conditions.

Generally, with a higher reaction temperature and a longer reaction time, red blood cells can be lysed more deeply. However, since any hemolytic agent will have an effect on any cell membrane, deep lysis (deep hemolysis) of red blood cells herein means that reaction conditions are selected to make red blood cells be further lysed as compared to a conventional condition, but cell morphologies of platelets can be basically maintained, and preferably cell morphologies of white blood cells can also be basically maintained. In the scatter diagram of light signals, platelets and lysed red blood cells can generate two distinct groups. In contrast, conventional lysis of red blood cells herein refers to a condition that a conventional hemolytic agent is used, and after reaction, the lysed red blood cells will be mixed in the platelet particle group.

As described in detail in the following specific examples, in the method of the first embodiment, red blood cells can be lysed more deeply so that the cell membranes of the red blood cells are broken into smaller fragments, thereby clearly differentiating the fragmented red blood cell region from the platelet region in a scatter diagram of the forward scattered light intensity and the side scattered light intensity obtained by optical detection, and achieving accurate and precise detection and counting of platelets. In addition, white blood cell subpopulations at least including monocytes, lymphocytes and neutrophils can also be obtained.

According to implementation, the blood sample treated with the first reagent is also treated with a second reagent.

The second reagent comprises a dye selected from a membrane-specific dye and a mitochondrion-specific dye, and/or comprises a nucleic acid-specific dye.

The membrane-specific dye may be selected from one or more of DiA, DiD, DiI, DiO, DiR, DiS, FDA, Alexa Fluor 488, Super Fluor 488 and variant structures using them as parents. Preferably, the membrane-specific dye is Alexa Fluor 488.

The mitochondrion-specific dye may be selected from one or more of Janus Green B, MitoLite Red, Rhodamine 123, Mitotracker series and their parents. Preferably, the mitochondrion-specific dye is Mitotracker Deep Red or Mitotracker Red.

In the present disclosure, variant structures of the dyes comprise commercial variant structures or non-commercial variant structures. According to the name, the structure and the like of the dyes, those skilled in the art can obtain variant structures (such as commercial variant structures) with known dyes as parents from the prior art; meanwhile, non-commercial variant structures can be obtained according to parent structures and/or existing variant structures, and it can be reasonably expected that these variant structures can achieve a staining effect similar to that of their parents. These variant structures all fall within the protection scope of the present disclosure.

In the present disclosure, the "membrane-specific dye" refers to a fluorescence dye capable of specifically staining blood platelet membranes. And similarly, "mitochondrion-specific dye" refers to a fluorescence dye capable specifically staining blood platelet mitochondrion. After the blood sample is treated with the first reagent and the second reagent containing a membrane-specific dye or a mitochondrion-specific dye, difference of fluorescence characteristics between platelets and lysed red blood cells becomes more significant, so that platelets can be further differentiated from the lysed red blood cell fragments by detecting the fluorescence intensity and at least one of the forward scattered light intensity and the side scattered light intensity, especially by detecting the fluorescence intensity and the forward scattered light intensity.

The first reagent in the first embodiment of the present disclosure comprises a surfactant having a strong hemolyzing capability, so that the red blood cells are lysed into smaller fragments. The number of organelle particles released from reticulocytes (RET) after hemolysis has a certain correlation with the value of RETs. As reticulocytes are red blood cells having nucleus, these particles can be specifically stained after a nucleic acid-specific fluorescence dye is added.

In addition, the applicant found in the study that for some blood samples containing a relatively large quantity of reticulocytes (RET), reticulocytes may interfere with platelets when the blood samples are simply detected by using forward scattered light signals and side scattered light signals. For this phenomenon, the above-mentioned second reagent containing a membrane or mitochondrion-specific dye can be used to alarm that reticulocytes exist. Specifically, particles in a preset region of a two-dimensional scatter diagram generated from forward scattered light signals and fluorescent signals may be counted, and when the count value exceeds a predetermined value (for example, the count value exceeds the number of platelets to a certain degree), an alarm for reticulocyte alarming may be given, so as to further examine the subject.

By adopting implementation, the above-mentioned three classifications or even four classifications of white blood cells can be obtained, and immature granulocytes can be identified as well.

According to one implementation, the second reagent may comprise a nucleic acid-specific dye, especially nucleic acid-specific dye for reticulocytes. In one implementation, the blood sample can be stained by using the nucleic acid dye, thereby not only obtaining information of reticulocytes, but also further differentiating platelets from organelle particles released after reticulocytes are lysed.

Therefore, the described implementation of the present disclosure is capable of further achieving effective measurements of reticulocytes while detecting platelets. In addition, the nucleic acid fluorescence dye can also be used for effectively staining white blood cell nuclei, and thus the classification detection of white blood cells can also be achieved by utilizing fluorescence signals.

The nucleic acid-specific dye used in the present disclosure is not particularly limited. Commercialized nucleic acid fluorescence dyes and nucleic acid-specific fluorescence dyes already disclosed in some patent applications may all be applied to the present disclosure. Examples of the commercialized nucleic acid fluorescence dyes are Thermofisher's SYTO series nucleic acid dyes. In addition, fluorescence dyes disclosed in Chinese Patent Application CN201010022414.6, anthocyanin dyes disclosed in CN200910109215.6, fluorescence dyes disclosed in CN200810216864.1, etc., may all be applied to the present disclosure. The entire contents of the above patent documents are incorporated herein by reference.

The concentration range of the nucleic acid dye varies according to the properties of the specifically used dyes, is not particularly limited, and is usually from 0.002 ppm to 2000 ppm. The preferred concentration range is from 0.03 ppm to 20 ppm.

The second reagent preferably further comprises an organic solvent. The organic solvent may be methanol, ethanol, glycerin, etc., but is not limited thereto.

In one implementation, the second reagent may comprise a membrane-specific dye or a mitochondrion-specific dye and comprise a nucleic acid-specific dyes, to obtain a more accurate and precise platelet count, as well as to obtain a white blood cell classification and count and a reticulocyte count at the same time.

In the above-mentioned method using the second reagent containing fluorescence dyes, platelets can be differentiated from other particles in the sample and platelets can be counted (the reticulocyte count can be obtained by using nucleic acid dyes) according to the fluorescence information and forward scattered light information. And the classification information and count of white blood cells are further obtained by utilizing the fluorescence information and side scattered light information. Further, the intensities of fluorescence, forward scattered light, and side scattered light can be simultaneously used to obtain a three-dimensional scatter diagram of volume distribution, thereby realizing the classification and counting of each particle.

The above-mentioned detailed first embodiment of the second blood detection method of the present method may be all applied to the first blood detection method of the present disclosure. Therefore, the first blood detection method according to the present disclosure will not be described in detail again.

According to a second embodiment of the present disclosure, a blood sample is treated with a first reagent and a second reagent to obtain a test sample.

In this embodiment, the first reagent comprises a hemolytic agent for lysing red blood cells. The hemolysis degree of the hemolytic agent is not particularly limited, and the hemolytic agent may be a conventional hemolytic agent. Exemplary hemolytic agents are, for example, quaternary ammonium cationic surfactants (such as tetradecyl trimethylammonium chloride), but the present disclosure is not limited thereto.

The second reagent comprises a dye selected from the above-mentioned membrane-specific dyes and mitochondrion-specific dyes.

In this embodiment, after the blood sample is treated with the first reagent containing a hemolytic agent and the second reagent containing a membrane-specific dye or a mitochondrion-specific dye, platelets and lysed red blood cells are significantly different in fluorescence characteristics, so that platelets can be commendably differentiated from the lysed red blood cell fragments by detecting the fluorescence intensity and the intensity of one type of scattered light, especially by detecting the fluorescence intensity and the forward scattered light intensity. Due to the use of the membrane-specific dye or the mitochondrion-specific dye, in this embodiment, red blood cells can be clearly differentiated from platelets by virtue of a two-dimensional scatter diagram just after being lysed by a hemolytic agent, without being deeply lysed as in the first embodiment. Moreover, in this implementation, the subpopulations and count of white blood cells can also be obtained by virtue of the fluorescence intensity information and the side scattered light intensity information, and an alarm is given when reticulocytes are present.

In this embodiment, the second reagent may further comprise a nucleic acid-specific dye. And accordingly, optical information of reticulocytes can thus be further obtained, and reticulocytes can be preferably counted.

In a third embodiment, the blood detection method of the present disclosure may further perform detection by adopting an optical detection system that eliminates the interference of the laser on pulse wave of platelet light signals, after the blood sample is lysed according to the aforementioned first embodiment or second embodiment, thereby obtaining a more accurate platelet count.

The laser in a conventional optical detection system is susceptible to the reflected light in an optical path and is thus unstable, resulting in amplitude changes, frequency shifts, or power peaks, etc. In practical applications, when power peaks are generated due to unstable oscillation of the laser, they appear in optical forward signals as small pulses. These interfering small pulses are confused with small pulses generated by platelet particles in detection, resulting in interference.

The optical detection system of the present disclosure is described in detail with reference to FIGS. 1-9.

During the research, the inventors have discovered that in order to prevent the reflected light from being fed back to the laser, a magneto-optical device based on the Faraday effect may be used as an optical isolator and placed in the optical path. This isolator has a relatively large mechanical size and generally can only be placed outside a light source assembly, while the light beam outside the light source assembly is non-parallel light, and when the non-parallel light enters the optical isolator, the optical isolation effect of the optical isolator will be seriously weakened. Therefore, this implementation has the disadvantages of large size, high cost, and poor isolation effect.

In an embodiment of the present disclosure, the optical detection system comprises an optical subsystem, a flow chamber and a first detector, and the optical subsystem comprises a laser, a front optical assembly comprising an optical isolator, and a rear optical assembly comprising a blocking diaphragm, wherein
- the laser is configured to emit a laser beam;
- the front optical assembly is configured to perform front optical treatment on the laser beam, so that the laser beam subjected to the front optical treatment is converged at the blocking diaphragm in a second direction and converged in a first direction at the blood cell sample to be tested in the flow chamber, and scattered light is thus generated;
- the rear optical assembly is disposed downstream of the flow chamber along the propagation direction of the laser beam, and is configured to perform rear optical treatment on the scattered light and the laser beam converged at the blocking diaphragm, so that the scattered light subjected to the rear optical treatment enters the first detector for light intensity detection;
- the optical isolator is configured to isolate reflected light generated by the laser beam when passing through the flow chamber and the rear optical assembly.

In the following, optical detection systems provided by embodiments of the present disclosure will be described in detail.

Figure 2:
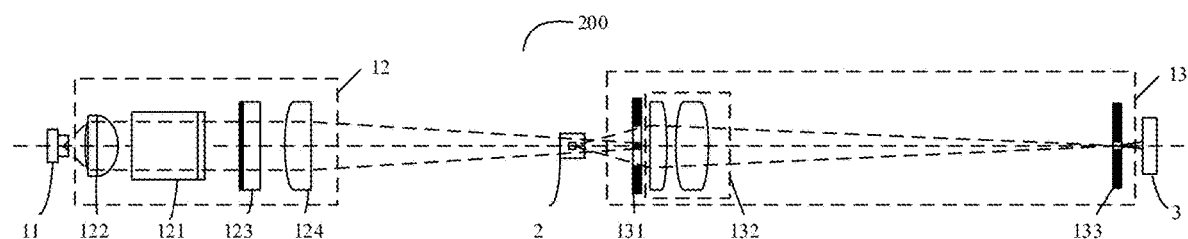
FIG. 2 illustrates a schematic structure diagram II of an optical detection system provided by an embodiment of the present disclosure.

FIG. 1 is a schematic structure diagram I of an optical detection system provided by an embodiment of the present disclosure, and FIG. 2 is a schematic structure diagram II of an optical detection system 200 provided by an embodiment of the present disclosure. With reference to FIGS. 1 and 2, the optical detection system 200 provided by the embodiment of the present disclosure comprises an optical subsystem 1, a flow chamber 2, and a first detector 3;
- the optical subsystem 1 comprises a laser 11, a front optical assembly 12 comprising an optical isolator 121, and a rear optical assembly 13 comprising a blocking diaphragm 131, wherein
- the laser 11 is configured to emit a laser beam;
- the front optical assembly 12 is configured to perform front optical treatment on the laser beam, so that the laser beam subjected to the front optical treatment is converged at the blocking diaphragm 131 in a second direction, and converged in a first direction at a blood cell sample to be tested in the flow chamber 2, and scattered light is thus generated;
- the rear optical assembly 13 is disposed downstream of the flow chamber 2 along the propagation direction of the laser beam, and is configured to perform rear optical treatment on the scattered light and the laser beam converged at the blocking diaphragm 131, so that the scattered light subjected to the rear optical treatment enters the first detector 3 for light intensity detection; and
- the optical isolator 121 is configured to isolate reflected light generated by the laser beam when passing through the flow chamber and the rear optical assembly.

Next, the laser 11 in the optical subsystem will be described. In an embodiment, the laser 11 is a semiconductor laser. In a practical implementation, the laser 11 may be a P-linearly polarization laser. In practical applications, the wavelength of the laser beam emitted by the laser determines the design of the main parameters of the optical path, such as the model selection of a lens, the selection of signal collection angle and the like, and the wavelength of the laser beam is also related to reagents such as fluorescence dyes used in the detection. In an embodiment, the wavelength of the laser beam emitted by the laser 11 is within 630 nm to 640 nm.

Next, each part of the front optical assembly 12 in the optical subsystem will be described.

In an embodiment, the optical isolator 121 in the front optical assembly 12 comprises a beam splitter prism and a polarization conversion element which are adhesively connected with each other;
- the beam splitter prism is configured to reflect the S-polarization component of the incident laser beam and transmit the P-polarization component of the incident laser beam;
- the polarization conversion element is configured to change the polarization state of the P-polarization component transmitted through the beam splitter prism, so that the P-polarization component is changed from linearly polarized light into circularly polarized light, and to change the polarization state of the circularly polarized light after reflection into S-polarized light so that the S-polarized light is reflected by the beam splitter prism.

Figure 3:
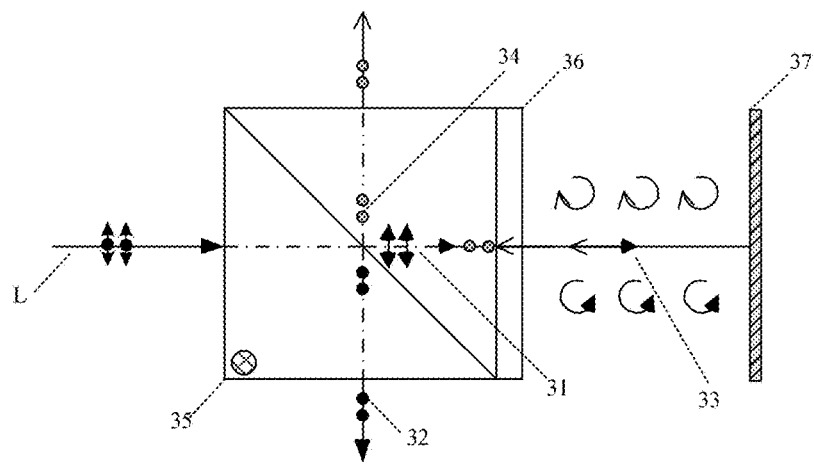
FIG. 3 illustrates a schematic diagram of an optical isolator provided by an embodiment of the present disclosure.

The polarization conversion element is a quarter wave plate, which is taken as an example, as shown in FIG. 3. FIG. 3 is a principle schematic diagram of an optical isolator provided by an embodiment of the present disclosure. When the laser beam L (TM mode) perpendicularly enters the beam splitter prism 35, the P-polarized light 31 (namely the polarization component parallel to the plane of the drawing) in the laser beam L can pass through the beam splitter prism 35, while the S-polarized light 32 (namely the polarization component perpendicular to the plane of the drawing) in the laser beam L is reflected by a 45-degree bevel of the beam splitter prism 35; afterwards, the P-polarized light 31 passes through the quarter wave plate 36, and the polarization state of the P-polarized light 31 passing through the quarter wave plate 36 is changed from linearly polarized light into circularly polarized light 33; the reflected light (reflected light reflected by the downstream optical path 37) of the circularly polarized light 33 passes through the quarter wave plate again and the polarization state is changed from circularly polarized light into S-polarized light 34, and the S-polarized light 34 will be reflected by the 45-degree bevel of the beam splitter prism 35 without being fed back to the laser, thereby realizing the isolation of the reflected light in the optical path.

Figure 4:
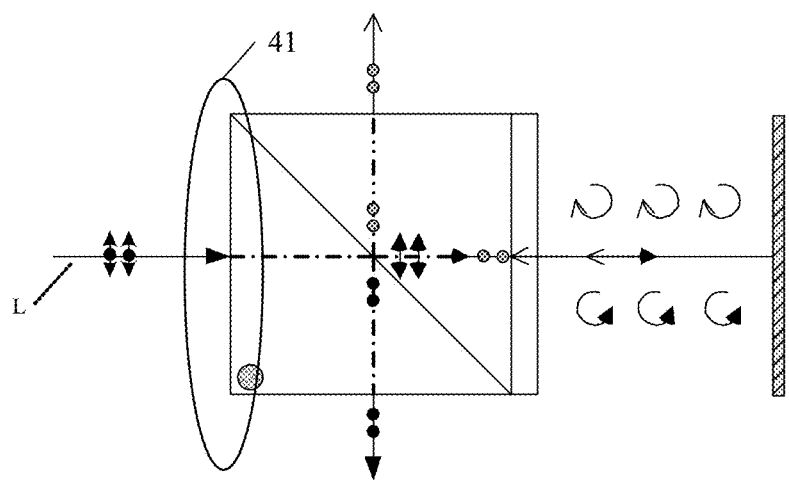
FIG. 4 illustrates a schematic diagram of a first incident surface of an optical isolator provided by an embodiment of the present disclosure.

Here, in practical applications, when the laser beam is perpendicularly incident to the optical isolator, the reflectivity of the first incident surface of the beam splitter prism is not greater than 0.5%, or not greater than 0.1%, or not greater than 0.05%. Herein, the first incident surface is shown in FIG. 4. FIG. 4 is a schematic diagram of the first incident surface of an optical isolator provided by an embodiment of the present disclosure, wherein the reference number 41 represents the first incident surface. In a practical implementation, the light reflectivity of the first incident surface can be achieved by the coating design and process of the first incident surface.

In an embodiment, the optical isolator 121 may also comprise a polarization analyzer and a polarization conversion element which are adhesively connected with each other;
- the polarization analyzer is configured to allow only the P-polarization component of the laser beam to pass through;
- the polarization conversion element is configured to change the polarization state of the P-polarization component passing through the polarization analyzer, so that the P-polarization component is changed from linearly polarized light into circularly polarized light, and to change the polarization state of reflected light of the circularly polarized light after reflection into S-polarized light so that the S-polarized light is isolated by the polarization analyzer.

As an example, the polarization conversion element is a magneto-optical crystal. When the laser beam enters the polarization analyzer, only the P-polarized light in the laser beam can pass through the polarization analyzer. After the P-polarized light passing through the polarization analyzer enters the magneto-optical crystal, the polarization state of the P-polarized light passing through the magneto-optical crystal is changed, and the polarization direction of the P-polarized light is rotated by 45°. The reflected light formed after the polarized light is reflected by the downstream optical path passes through the magneto-optical crystal again, and the polarization direction is rotated by 45° again, thereby forming S-polarized light perpendicular to the polarization state of the original P-polarized light so that the S-polarized light is isolated by the polarization analyzer without being fed back to the laser.

In practical applications, the polarization conversion element may also be a rotary optical crystal. In practical applications, the beam splitter prism and the polarization analyzer can be combined with any one of the quarter wave plate, the magneto-optical crystal and the rotary optical crystal to achieve the isolation of the reflected light in the optical path.

In an embodiment, the optical isolator 121 comprises a bandpass filter and a frequency-doubling crystal which are adhesively connected with each other;
- the bandpass filter is configured to allow the laser beam with a wavelength λ to pass through;
- the frequency-doubling crystal is configured to perform frequency doubling on the laser beam passing through the bandpass filter and perform frequency doubling again on reflected light of the frequency-doubled laser beam, so that the reflected light is filtered out by the bandpass filter.

In an embodiment, the optical isolator has an optical isolation degree not smaller than 30 db.

In an embodiment, the front optical assembly 12 further comprises a collimating lens 122;
- the collimating lens 122 is disposed between the laser 11 and the optical isolator 121 along the propagation direction (the direction of the optical axis) of the laser beam and is configured to collimate the laser beam to make the laser beam become a parallel beam.

In an embodiment, the front optical assembly 12 further comprises a first light converging element 123 and a second light converging element 124;
- the first light converging element 123 is configured to perform first focusing on the laser beam so that the laser beam is converged in the first direction at the blood cell sample to be tested in the flow chamber, and scattered light is thus generated;
- the second light converging element 124 is configured to perform second focusing on the laser beam so that the laser beam is converged at the blocking diaphragm 131 in the second direction.

Here, in practical applications, the second direction is the transverse direction, namely a direction perpendicular to the flow direction of the blood cell sample to be tested; and the first direction is the longitudinal direction, namely a direction the same as the flow direction of the blood cell sample to be tested. In practical applications, the first light converging element 123 and the second light converging element 124 may be implemented by cylindrical lenses with different optical parameters (such as focal length, etc.), for example, the first light converging element 123 is implemented by a first cylindrical lens, and the second light converging element 124 is implemented by a second cylindrical lens.

Figure 5:
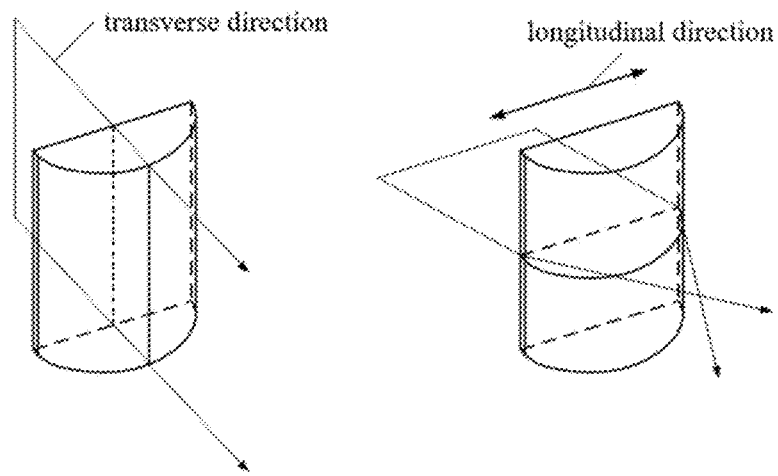
FIG. 5 illustrates a light converging schematic diagram of a second cylindrical lens provided by an embodiment of the present disclosure.

The second light converging element 124 is a second cylindrical lens, which is taken as an example for description, as shown in FIG. 5. FIG. 5 is a light converging schematic diagram of a second cylindrical lens provided by an embodiment of the present disclosure. The laser beam passes through the second cylindrical lens and is not treated in the longitudinal direction by the second cylindrical lens; the laser beam passing through the second cylindrical lens is compressed in the transverse direction and the laser beam is focused in the transverse direction (perpendicular to the flow direction of the blood cell sample to be tested), and focused at the blocking diaphragm in the embodiment of the present disclosure.

Figure 6:
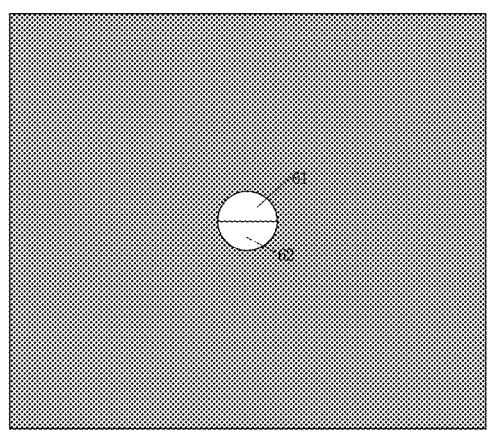
FIG. 6 illustrates a front view of a blocking diaphragm provided by an embodiment of the present disclosure.

Next, each part of the rear optical assembly 13 will be described, as shown in FIG. 6. FIG. 6 is a front view of a blocking diaphragm provided by an embodiment of the present disclosure. The laser beam irradiated on the blood cell sample in the flow chamber is scattered, and the generated scattered light is collected by the blocking diaphragm. In a practical implementation, the blocking diaphragm is used to restrict the collection angle of low angle scattering signals, and the blocking diaphragm is also used to stop the laser beam converged at the blocking diaphragm in the second direction. In an embodiment, the light collection angle of the blocking diaphragm may be 1-10°.

In an embodiment, the rear optical assembly 13 further comprises a third converging element 132 and an aperture diaphragm 133;

the third converging element 132 is configured to perform third focusing on the scattered light so that the scattered light is converged at the aperture diaphragm and enters the first detector via the aperture of the aperture diaphragm, for light intensity detection.

In an embodiment, the third converging element may be one of the followings:

a lens assembly including at least one plano-convex lens and at least one biconvex lens;
a lens assembly including at least two plano-convex lenses;
a lens assembly including at least two biconvex lenses;
a lens assembly including at least two spherical lenses; and an aspherical lens.

In an embodiment, the optical detection system further comprises a second detector 4 and a fluorescence detector 5;

the second detector is disposed in a direction which forms an angle within a preset angle range with the propagation direction of the laser beam, and is configured to perform light intensity detection on the scattered light which forms an angle within the preset angle range with the propagation direction of the laser beam;
and the fluorescence detector is disposed in a direction which forms an angle within a preset angle range with the propagation direction of the laser beam, and is configured to perform fluorescence detection on fluorescence generated by the blood cell sample to be tested.

Figure 7:
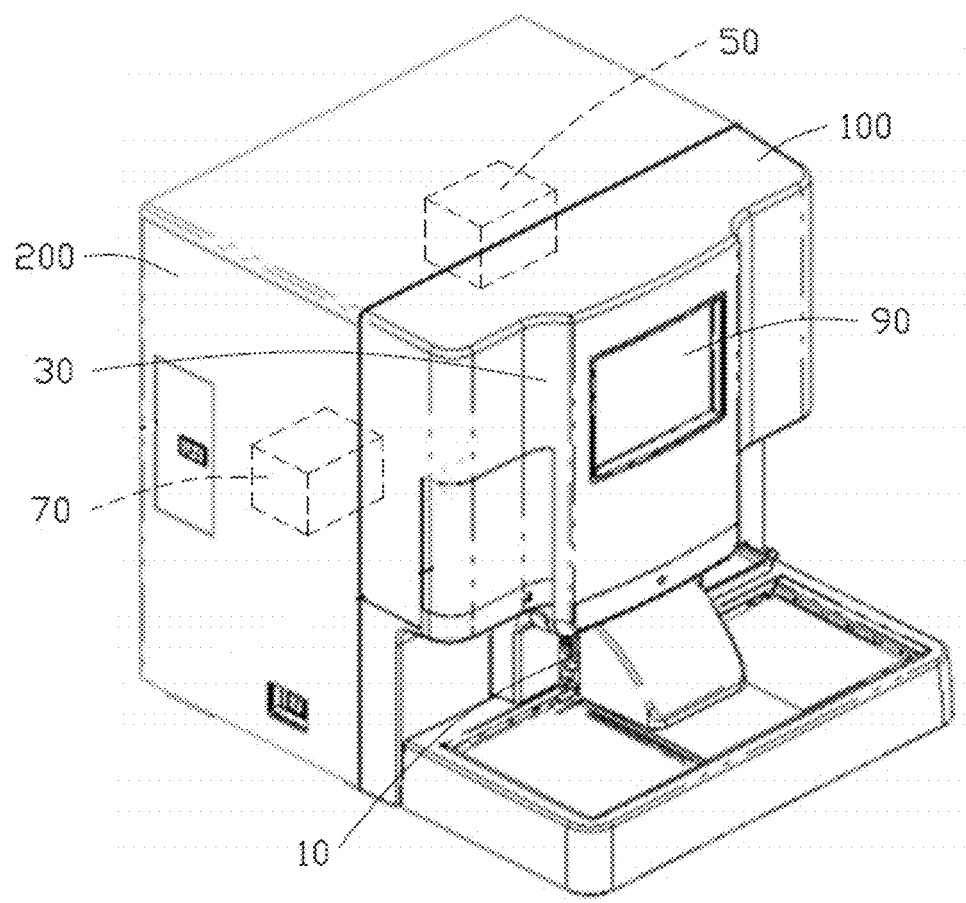
FIG. 7 illustrates a schematic structure diagram of a blood cell analyzer provided by an embodiment of the present disclosure.

Next, a blood analysis system provided by an embodiment of the present disclosure will be described, and FIG. 7 is a schematic structure diagram of a blood analysis system provided by an embodiment of the present disclosure. The blood analysis system according to the present disclosure generally comprises a sampling part, a reagent supply part, a reaction part, an optical detection system, and a data processing part.

FIG. 7 illustrates a specific blood analysis system according to the present disclosure. The blood analysis system comprises a first housing 100, a second housing 200, a sampling part 10, a reagent supply part (not shown), a reaction part 30, an optical detection system 50, a data processing part 70 and an output part 90. In practical applications, the output part 90 may be a user interface. In this embodiment, the optical detection system 50 and the data processing part 70 are disposed inside the second housing 200 and are disposed on both sides of the second housing 200 respectively. The reaction part 30 is disposed inside the first housing 100, and the output part 90 and the sampling part 10 are disposed on an outer surface of the first housing 100.

The sampling part 10 comprises a sampling needle for collecting a blood sample and conveying the collected blood sample to the reaction part 30.

The reagent supply part is used for storing a reagent (for example at least storing the aforementioned first reagent) reacting with the blood sample and supplying the corresponding reagent to the reaction part as needed.

The reaction part 30 is configured to make the blood sample from the sampling part react with the reagent from the reagent supply part to obtain a test sample solution containing a plurality of platelet particles, so that the platelet particles are flowed through a flow chamber of the optical detection system one by one.

The optical detection system 50 comprises an optical subsystem, a flow chamber and a first detector. The optical subsystem comprises a laser, a front optical assembly, and a rear optical assembly, and the front optical assembly comprises an optical isolator. The laser is configured to emit a laser beam; the front optical assembly is configured to perform front optical treatment on the laser beam, so that the laser beam subjected to the front optical treatment is converged at blood particles (such as platelet particles) in the flow chamber in a first direction and scattered light is thus generated; the rear optical assembly is disposed downstream of the flow chamber in the propagation direction of the laser beam, and is configured to perform rear optical treatment on the scattered light, so that the scattered light subjected to the rear optical treatment enters the first detector for light intensity detection; the optical isolator is configured to isolate reflected light from the laser, wherein the reflected light is generated when the laser beam passes through the flow chamber and the rear optical assembly. The flow chamber allows blood particles such as platelet particles to pass through in a line. The first detector is used for detecting optical information, especially light intensity information of the blood particles passing through the flow chamber.

The data processing part 70 is configured to detect blood particles (for example, platelets) flowing through the flow chamber according to a light intensity signal of the scattered light detected by the first detector, to obtain a detection result corresponding to the blood particles.

The output part 90 is configured to output the detection result corresponding to the blood particles (for example, platelets).

Next, each part included by the optical detection system 50 of the blood analysis system will be described.

Figure 8:
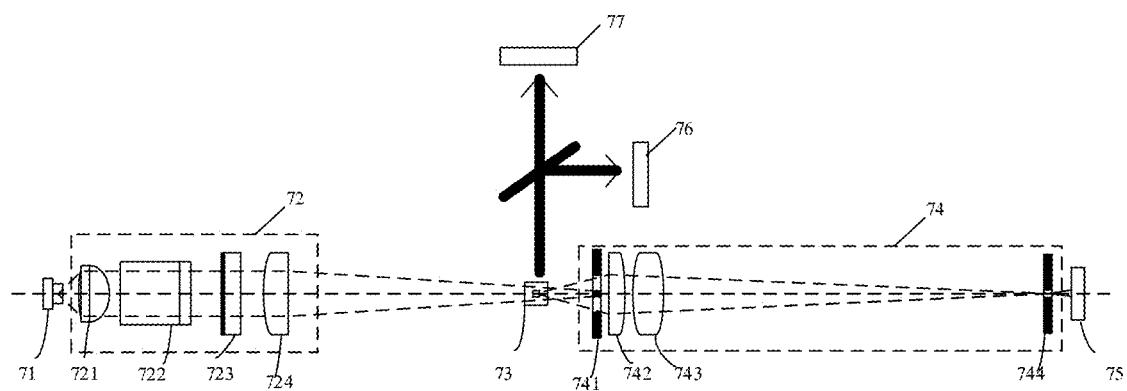
FIG. 8 illustrates a schematic structure diagram III of an optical detection system provided by an embodiment of the present disclosure.

FIG. 8 is a schematic structure diagram of an optical detection system provided by an embodiment of the present disclosure. As shown in FIG. 8, the optical detection system provided by the embodiment of the present disclosure comprises a laser 71, a front optical assembly 72, a flow chamber 73, and a rear optical assembly 74, a forward detector 75, a side detector 76, and a fluorescence detector 77.

In practical applications, blood particles (especially taking platelet particles as an example) pass through the flow chamber and are detected (such as detected in terms of light intensity), counted, etc. In this embodiment, the flow direction of the platelet particles is a direction perpendicular to the plane of the drawing, and the propagation direction of the laser beam emitted by the laser 71 is a direction parallel to the plane of the drawing.

In a practical implementation, the laser 71 is a P-linearly polarization laser, and the wavelength of the laser beam emitted by the laser 71 is within 630 nm to 640 nm.

As shown in FIG. 8, the front optical assembly 72 comprises a collimating lens 721, an optical isolator 722, a first cylindrical lens 723 and a second cylindrical lens 724 that are sequentially disposed in the propagation direction of the laser beam. The rear optical assembly 74 comprises a blocking diaphragm 741, a plano-convex lens 742, a biconvex lens 743 and an aperture diaphragm 744 that are sequentially disposed in the propagation direction of the laser beam.

The laser beam emitted by the laser 71 is collimated by the collimating lens 721 to become a parallel laser beam, then passes through the optical isolator 722, and is focused at the center of the flow chamber 73 in the longitudinal direction (perpendicular to the plane of the drawing) by the first cylindrical lens 723 to form a detection light spot. The propagation direction of the laser beam is perpendicular to the light incident surface of the flow chamber. The laser beam focused at the flow chamber is irradiated on the platelet particles in the flow chamber and is thus scattered. After being compressed in the longitudinal direction by the first cylindrical lens 723, the size of the laser beam in the longitudinal direction is matched with that of platelet particles. The laser beam passing through the first cylindrical lens 723 enters the second cylindrical lens 724, and is compressed in the transverse direction (parallel to the plane of the drawing), and is converged in the transverse direction at the blocking diaphragm 741.

Wherein, the scattered light generated by the platelet particles irradiated in the flow chamber is collected by the blocking diaphragm, so that the scattered light is focused by a lens assembly consisting of the plano-convex lens 742 and the lenticular lens 743, then converged at the aperture diaphragm 744 and enters the forward detector 75 via the aperture of the aperture diaphragm 744 so as to be detected in terms of forward light signal intensity by the forward detector 75.

In practical applications, as shown in FIG. 8, the side detector 76 and the fluorescence detector 77 are disposed along a direction perpendicular to the propagation direction of the laser beam, wherein the side detector 76 is configured to perform light intensity detection on the scattered light perpendicular to the propagation direction of the laser beam, and the fluorescence detector 77 is disposed along a direction perpendicular to the propagation direction of the laser beam and is configured to perform fluorescence detection on the scattered light.

In a practical implementation, the laser beam emitted by the laser 71 will be reflected when propagating in the optical path shown in FIG. 8, and the optical isolator 722 is configured to isolate the reflected light generated by the laser beam emitted by the laser 71 when the laser beam propagates in the optical path.

In an embodiment, the optical isolator 722 comprises a beam splitter prism and a quarter wave plate which are adhesively connected with each other;

the beam splitter prism is configured to reflect the S-polarization component of the incident laser beam and transmit the P-polarization component of the incident laser beam;

the quarter wave plate is configured to change the polarization state of the P-polarization component transmitted through the beam splitter prism, so that the P-polarization component is changed from linearly polarized light into circularly polarized light, as well as to change the polarization state of the circularly polarized light after reflection into S-polarized light so that the S-polarized light is reflected by the beam splitter prism.

When the laser beam perpendicularly enters the beam splitter prism, the P-polarized light (namely the polarization component parallel to the plane of the drawing) in the laser beam can pass through the beam splitter prism, while the S-polarized light (namely the polarization component perpendicular to the plane of the drawing) in the laser beam is reflected by a 45-degree bevel of the beam splitter prism; afterwards, the P-polarized light passes through the quarter wave plate, and the polarization state of the P-polarized light passing through the quarter wave plate is changed from linearly polarized light into circularly polarized light; the reflected light (reflected light reflected by the downstream optical path) of the circularly polarized light passes through the quarter wave plate again and the polarization state is changed from the circularly polarized light to S-polarized light; and the S-polarized light will be reflected by the 45-degree bevel of the beam splitter prism without being fed back to the laser, thereby realizing the isolation of the reflected light in the optical path.

Here, in practical applications, when the laser beam perpendicularly enters the optical isolator, the reflectivity of the first incident surface of the beam splitter prism is not greater than 0.5%. Herein, the first incident surface is shown in FIG. 4. FIG. 4 is a schematic diagram of a first incident surface of an optical isolator provided by an embodiment of the present disclosure, wherein the surface represented by the reference number 41 is the first incident surface. In a practical implementation, the light reflectivity of the first incident surface can be achieved by the coating design and process of the first incident surface.

In an embodiment, the optical isolator 121 may also comprise a polarization analyzer and a polarization conversion element which are adhesively connected with each other;

the polarization analyzer is configured to allow only the P-polarization component of the laser beam to pass through;

and the magneto-optical crystal is configured to change the polarization state of the P-polarization component passing through the polarization analyzer so that the polarization direction of the P-polarization component is rotated by 45°. The reflected light formed after the polarized light is reflected by the downstream optical path passes through the magneto-optical crystal again, and the polarization direction is rotated by 45° again, thereby forming S-polarized light perpendicular to the polarization state of the original P-polarized light so that the S-polarized light is isolated by the polarization analyzer.

When the laser beam enters the polarization analyzer, only the P-polarized light in the laser beam can pass through the polarization analyzer, the P-polarized light passing through the polarization analyzer enters the magneto-optical crystal, the polarization state of the P-polarized light passing through the magneto-optical crystal is changed, and the polarization direction of the P-polarized light is rotated by 45°. The reflected light formed after the polarized light is reflected by the downstream optical path passes through the magneto-optical crystal again, and the polarization direction is rotated by 45° again, thereby forming S-polarized light perpendicular to the polarization state of the original P-polarized light so that the S-polarized light is isolated by the polarization analyzer without being fed back to the laser.

In an embodiment, the optical isolator may also comprise a bandpass filter and a frequency-doubling crystal which are adhesively connected with each other;

the bandpass filter is configured to allow the laser beam with a wavelength λ to pass through;

the frequency-doubling crystal is configured to perform frequency doubling on the laser beam passing through the bandpass filter and perform frequency doubling again on reflected light of the frequency-doubled laser beam, so that the reflected light is filtered out by the bandpass filter.

In an embodiment, the optical isolator has an optical isolation degree not smaller than 30 db.

Figure 9:
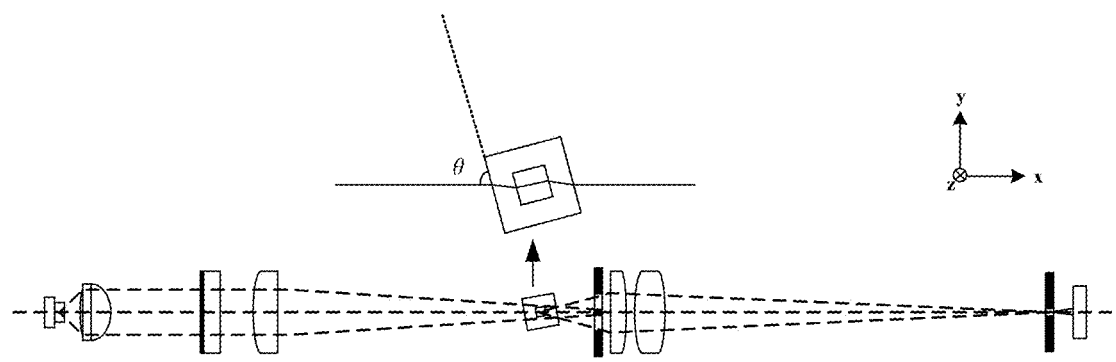
FIG. 9 illustrates a schematic structure diagram IV of an optical detection system provided by an embodiment of the present disclosure.

In an embodiment, the included angle between the propagation direction of the laser beam and the light incident surface of the flow chamber may be a non-perpendicular angle, namely the position of the flow chamber in the above-mentioned embodiments is deflected by a certain angle in the x-y plane, namely in the plane of drawing so that the flow chamber is obliquely disposed. FIG. 9 is a schematic structure diagram of an optical detection system provided by an embodiment of the present disclosure. As shown in FIG. 9, the included angle θ between the propagation direction of the laser beam and the light incident surface of the flow chamber is an acute angle. In an embodiment, the angle θ ranges from 80° to 90°. Thus, when the laser beam irradiates the inside of the flow chamber, after the light beam is reflected on the inner surface of the flow chamber, the reflected light is deviated from the optical axis (the propagation direction of laser beam), thereby reducing the luminous flux of the reflected light entering the laser. Those skilled in the art can understand that any angle θ is applicable to the present application as long as it would not cause the light reflected on the light incident surface of the flow chamber to enter the front optical module. Through in-depth researches, it was found that although the oblique placement of the flow chamber may cause deviation of the optical path of forward scattered light and change of the collection angles of fluorescence and side scattered light, by further in-depth researches, it was found that it is possible to compensate for the influence of the forward scattered light by adjusting the position of the rear optical assembly in the optical path, and meanwhile, it has been proved through a large number of research experiments that this is acceptable for the detection of the fluorescence and side scattered light, without affecting final detection results.

In the above-mentioned embodiments of the present disclosure, platelet particles are relatively small and generate small pulses when flowing through the flow chamber, as the reflected light generated by the laser beam when propagating in the optical path can be commendably isolated by the optical isolator in the optical detection system in the above-mentioned blood cell analyzer, the laser can stably output a laser beam, thereby avoiding small pulses occurring due to power peaks generated when the reflected light enters the laser, also avoiding confusion between the interfering small pulses and the small pulses generated by platelet particles, and greatly improving the detection precision.

An embodiment of the present disclosure also provides a platelet detection method applied to the above-mentioned blood cell analyzer comprising an optical detection system, wherein the optical detection system comprises a laser, a front optical assembly comprising an optical isolator, a rear optical assembly, a flow chamber and a first detector. The method comprises:

providing a test sample solution containing platelets;

making platelet particles in the test sample solution pass through a detection area of the flow chamber one by one;

performing front optical treatment on a laser beam emitted by the laser by using the front optical assembly so that the laser beam subjected to the front optical treatment is converged at the detection area of the flow chamber in a first direction and scattered light is generated when the platelet particles pass through the detection area;

performing rear optical treatment on the scattered light by using the rear optical assembly so that the scattered light subjected to the rear optical treatment enters the first detector;

wherein reflected light generated when the laser beam passes through the flow chamber and the rear optical assembly is isolated by the optical isolator; and performing light intensity detection on the incident scattered light by using the first detector to obtain a first detection result, so as to identify the platelet particles based on the first detection result.

In an embodiment, the method further comprises:

performing hemolysis treatment on the collected blood sample, so that red blood cells in the blood sample are lysed to obtain a test sample solution containing a plurality of platelet particles.

In an embodiment, the method further comprises:

performing front optical treatment on the laser beam by using the front optical assembly so that the laser beam subjected to the front optical treatment is converged at a blocking diaphragm included by the rear optical assembly in a second direction.

In an embodiment, the blood cell analyzer further comprises a second detector; correspondingly, the method further comprises:

performing light intensity detection on the scattered light which forms an angle within a preset angle range with the propagation direction of the laser beam to obtain a second detection result, thereby identifying the platelet particles based on the first detection result and the second detection result.

In an embodiment, the blood cell analyzer further comprises a fluorescence detector; correspondingly, the method further comprises:

performing staining treatment on the platelet particles in the test sample solution by using a specific fluorescence dye, wherein the specific fluorescence dye may be at least one of a membrane dye and a mitochondrion dye;

fluorescence is also generated when the platelet particles in the test sample solution pass through the detection area, and the fluorescence detector is configured to detect the fluorescence generated by the platelet particles to obtain a third detection result, thereby identifying the platelet particles based on the first detection result and the third detection result.

In an embodiment, the blood cell analyzer further comprises a second detector and a fluorescence detector; correspondingly, the method further comprises:

performing fluorescence staining treatment on the platelet particles in the test sample solution;

fluorescence is also generated when the platelet particles in the test sample solution pass through the detection area;

the second detector is configured to perform light intensity detection on the scattered light which forms an angle within a preset angle range with the propagation direction of the laser beam to obtain a second detection result, wherein the preset angle range may be 60° to 120°.

The fluorescence detector is configured to detect the fluorescence generated by the platelet particles to obtain a third detection result;

the platelet particles are identified, and white blood cell count and classification are obtained based on the first detection result, the second detection result and the third detection result.

By applying the above-mentioned embodiments of the present disclosure, the reflected light generated when the laser beam propagates in the optical path can be commendably isolated so that the laser can stably output a laser beam, thereby avoiding small pulses occurring due to power peaks generated when the reflected light enters the laser, and also avoiding confusion between the interfering small pulses and the small pulses generated by platelet particles when the blood cells to be tested are platelets, and greatly improving the detection precision of the blood cell analyzer.

The present disclosure and its advantages will be further described below through specific examples.

Example 1 Detection of Platelets by Deeply Hemolyzing

A hemolytic agent of the present disclosure was prepared according to the following formula:

| Decyl Glucoside | 0.6 g/L |
| --- | --- |
| TRIS | 70 Mm |
| Sodium Citrate | 6 g/L |
| Polyoxyethylene (23) Cetyl Ether | 0.5 g/L |
| PH | 7.5 |

Figure 10:
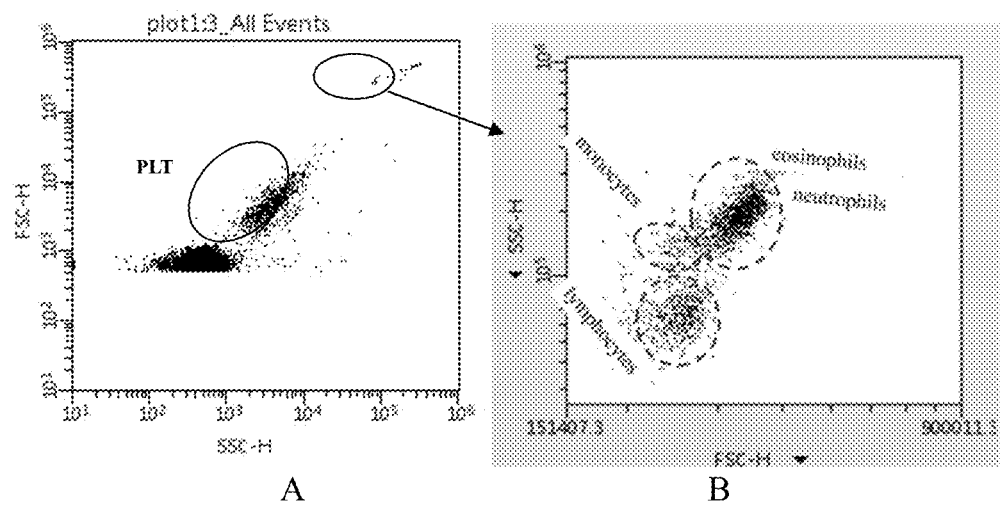
FIG. 10 illustrates a scatter diagram of platelets (A) and while blood cells (B) collected on a flow cytometer from a deeply-hemolyzed sample obtained in Example 1.

20 μl of a fresh blood sample was added into 1 mL of the above-mentioned prepared solution, incubation was performed at 45° C. for 60 seconds to prepare a test sample, and then detection was performed by adopting a flow cytometer (Mindray BriCyte E6). Data was collected and the gain was set as 500, the side scattered light with a measurement angle of 90 degrees was collected to obtain side scattered light intensity information of particles in the test sample; and forward scattered light signals of 0 degree were collected. A scatter diagram of platelets and white blood cells is shown in FIG. 10. From FIG. 10, it can be seen that red blood cell fragments, platelets and white blood cells are very different, and these three groups of particles can be clearly differentiated, and platelets and white blood cells can be effectively classified and counted simultaneously. By calculating the ratios of the divided white blood cells and PLT in combination with the injection volume of the flow cytometer, the concentration of white blood cells and PLT of this sample can be calculated to be 9.8×109/L and 166×109/L, respectively.

The concentration of white blood cells in the same sample measured by a Beckman particle counter Z2 was 9.6×109/L; the concentration of PLT measured by adopting manual microscopic examination counting was 171×109/L. The platelet count and the white blood cell count obtained by the method of the present disclosure have a relatively good consistency with the measurement results of the traditional methods.

Example 2 Comparison Between Deep Hemolysis and Conventional Hemolysis on Display State of Platelets A detection reagent of the present disclosure was prepared according to the following formula:

| Alkyl glycoside (APG0810) | 0.4 g/L |
| --- | --- |
| TRIS | 40 Mm |
| Sodium Citrate | 5 g/L |
| Polyoxyethylene (23) Cetyl Ether | 0.5 g/L |
| PH | 7.5 |

20 μl of a fresh blood sample was added into 1 mL of the solution prepared according to the above-mentioned formula, incubation was performed at 45° C. for 60 seconds, and then detection was performed by adopting a flow cytometer (Mindray BriCyte E6). The excitation wavelength was set as 488 nm, the gain was as 500, 0° forward scattered light intensity information and 90° side scattered light intensity information were collected to obtain a two-dimensional cell scatter diagram, as shown in A of FIG. 11.

For contrast, 20 μl of the same fresh blood sample was added into 1 mL of a LD hemolytic agent (which contains a conventional hemolytic agent) used in a Mindray blood analyzer BC-6800, incubation was performed at 45° C. for 60 seconds, and then detection was performed by adopting the flow cytometer (Mindray BriCyte E6). The excitation wavelength was set as 488 nm, the gain was set as 500, 0° forward scattered light intensity information and 90° side scattered light intensity information were collected to obtain a two-dimensional cell scatter diagram, as shown in B of FIG. 11.

Figure 11:
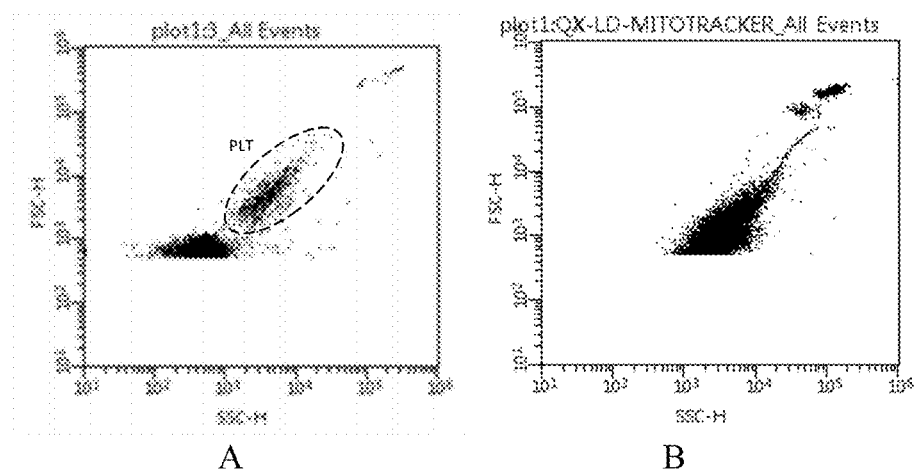
FIG. 11 illustrates a diagram showing the PLT comparison between a deeply-hemolyzed sample (A) of Example 2 and a sample (B) hemolyzed by a conventional hemolytic agent.

By comparing the two diagrams A and B in FIG. 11, it can be clearly seen that platelets (particle cluster in the middle) can be clearly differentiated from a region of fragmented red blood cells (particle cluster in the lower left) after the blood sample is treated with deep hemolysis by the method of the present disclosure (A), while blood ghost and platelets cannot be differentiated in a sample which is treated with the conventional hemolytic agent.

Example 3 Deeply Hemolyzing and Adding a Nucleic Acid Dye to Count Platelets and White Blood Cells by Side Scattered Light Signals and Fluorescence Signals A detection reagent of the present disclosure was prepared according to the following formula:

| | |
|---|---|
| Fluorescence Dye SYTO9 (Thermofisher Inc.) | 1.0 ppm |
| Dodecyl Maltoside | 0.6 g/L |
| TRIS | 40 Mm |
| Sodium Citrate | 5 g/L |
| Polyoxyethylene (23) Cetyl Ether | 0.5 g/L |
| PH | 7.5 |

20 μl of a fresh blood sample was added into 1 mL of the solution prepared according to the above-mentioned formula, incubation was performed at 45° C. for 60 seconds, and then detection was performed by adopting a flow cytometer (Mindray BriCyte E6). The excitation wavelength was set as 488 nm, the gain was set as 500, 90° side fluorescence intensity information and 0° forward scattered light intensity information were collected to obtain a two-dimensional cell scatter diagram, as shown in FIG. 12A.

It can be seen from the figure that in a hemolysis condition, by adding a nucleic acid dye, platelets and RET can be effectively differentiated and displayed in the fluorescence direction. The PLT concentration of this sample can be calculated to be 198×109/L according to the ratios of the divided PLT scatter dots and the injection volume of the flow cytometer. The PLT concentration calculated by adopting a manual microscopic examination method is 202×109/L. Platelets and red blood fragments can be effectively differentiated by the nucleic acid staining method of this example.

Besides, the method of this example has no effects on classification and counting of white blood cells. The same treatment is performed on another 20 μl of the same blood sample, and measurement was performed in the same flow cytometer. The excitation wavelength was set as 488 nm, the gain was set as 100,000, and 90° side fluorescence intensity information and 90° side scattered light intensity information were collected to obtain a two-dimensional cell scatter diagram, as shown in FIG. 12B. It can be seen from the figure that the dye is also capable of effectively staining white blood cells while staining PLT, and while blood cells can be clearly grouped. The WBC concentration of this sample can be calculated to be 7.86×109/L according to the ratio of the divided WBC scatter dots in combination with the injection volume of the flow cytometer. The WBC concentration of the same sample measured by using a traditional reference method combined with a Beckman particle counter depth Z2 was 8.01×109/L. The two methods have a relatively good consistency therebetween.

Figure 12:
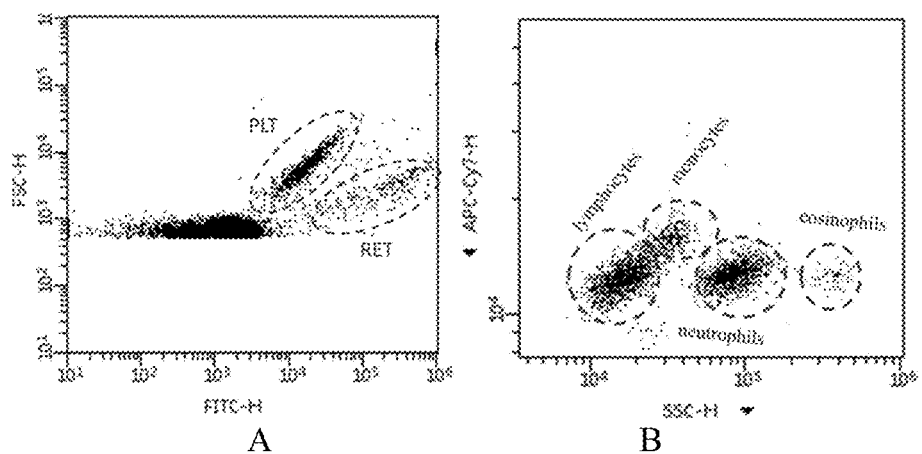
FIG. 12 illustrates a fluorescence-forward scattered light intensity scatter diagram (A) obtained by detecting platelets and reticulocytes under a deep hemolysis condition of Example 3, and a fluorescence-side scattered light intensity scatter diagram (B) of white blood cells.

By dividing lymphocytes, monocytes, neutrophils plus basophils, and eosinophils in FIG. 12B, the obtained ratios of them were 21.2%, 3.5%, 74.8%, and 0.5%, respectively. After this sample was tested on the Mindray blood cell analyzer 6800, the obtained ratios of lymphocytes, monocytes, neutrophils plus basophils, and eosinophils were 20.8%, 3.2%, 75.1%, and 0.9%, respectively. The above-mentioned results show that the white blood cell division performed by the method of the present disclosure has a relatively good correlation with the ratios obtained by the commercially available blood cell analyzer.

Example 4 Deeply Hemolyzing and Adding a Nucleic Acid Dye to Count Platelets, Reticulocytes and White Blood Cells by Light Scattering and Fluorescence Signals A detection reagent of the present disclosure was prepared according to the following formula:

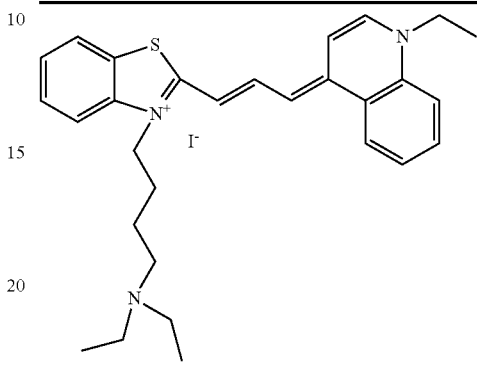

20 μl of a fresh blood sample was added into 1 mL of the solution prepared according to the above-mentioned formula, incubation was performed at 45° C. for 60 seconds, and then detection was performed by adopting a flow cytometer (Mindray BriCyte E6). The excitation wavelength was set as 633 nm, the gain was set as 500, and 90° side fluorescence intensity information and 0° forward scattered light intensity information were collected to obtain a two-dimensional cell scatter diagram, as shown in FIG. 13A.

As shown in the figure, RET and PLT can be clearly differentiated by fluorescence and forward scattered light signals, respectively. The PLT concentration of this sample can be calculated to be 165×109/L, and the RET concentration of this sample can be calculated to be 18.8×109/L according to the ratios of the divided PLT and RET scatter dots in combination with the injection volume of the flow cytometer. The numerical value of PLT detected by adopting a traditional manual microscopic examination was 175×109/L, and the concentration of RET was 20.1×109/L. It is proved that PLT and RET in the blood sample can be effectively differentiated and counted by the method of the present disclosure.

The same treatment was performed on another 20 μl of the same blood sample, and measurement was performed in the same flow cytometer. The excitation wavelength was set as 633 nm, the gain was set as 100,000, and 90° side fluorescence intensity information and 90° side scattered light intensity information were collected to obtain a two-dimensional cell scatter diagram, as shown in FIG. 13B.

Figure 13:
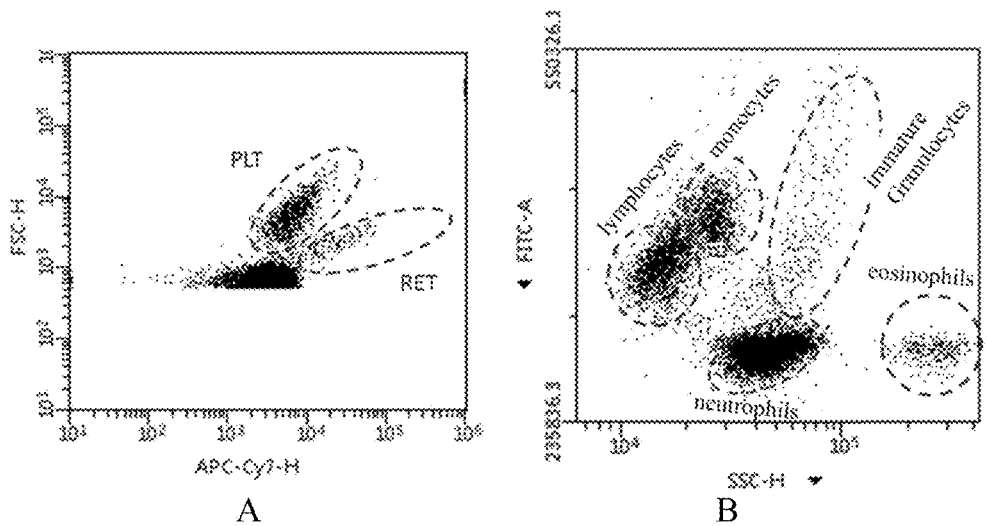
FIG. 13 illustrates a fluorescence-forward scattered light intensity scatter diagram (A) obtained by detecting platelets and reticulocytes under a deep hemolysis condition of Example 4, and a fluorescence-side scattered light intensity scatter diagram (B) of white blood cells.

As seen in FIG. 13B, white blood cells can be clearly divided into four types, including lymphocytes, monocytes, neutrophils plus basophils, and eosinophils. The WBC concentration of this sample can be calculated to be 8.32×109/L according to the ratio of the divided WBC scatter dots in combination with the injection volume of the flow cytometer. The WBC concentration of the same sample measured by using a traditional reference method combined with a Beckman particle counter Z2 was 8.45×109/L. It can be seen that the two methods have a relatively good consistency therebetween.

By dividing lymphocytes, monocytes, neutrophils plus basophils, eosinophils and immature granulocytes, the obtained ratios of them were 15.1%, 6.1%, 75.5%, 2.3%, and 1.0%, respectively. After this sample was tested on the Mindray blood cell analyzer 6800, the obtained ratios of lymphocytes, monocytes, neutrophils plus basophils, eosinophils and immature granulocytes were 14.8%, 5.7%, 76.2%, 1.9%, and 1.4%, respectively. The above-mentioned results show that the white blood cell division performed by the method of the present disclosure has a relatively good correlation with the ratios obtained by the commercially available blood cell analyzer.

Example 5 Deeply Hemolyzing and Adding a Nucleic Acid Dye to Detect Platelets and White Blood Cells by Light Scattering and Fluorescence Signals A detection reagent of the present disclosure was prepared according to the following formula:

| | |
|---|---|
| Fluorescence Dye (Structural Formula is as follows) | 1.0 ppm |
| Dodecyl Maltoside | 0.6 g/L |
| TRIS | 40 Mm |
| Sodium Citrate | 5 g/L |
| Polyoxyethylene (23) Cetyl Ether | 0.5 g/L |
| PH | 7.5 |
| Structural Formula of Fluorescence Dye: | |

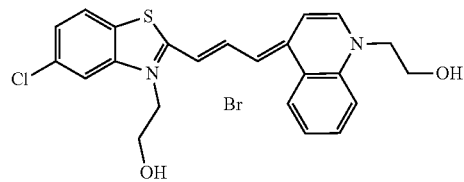

Figure 14:
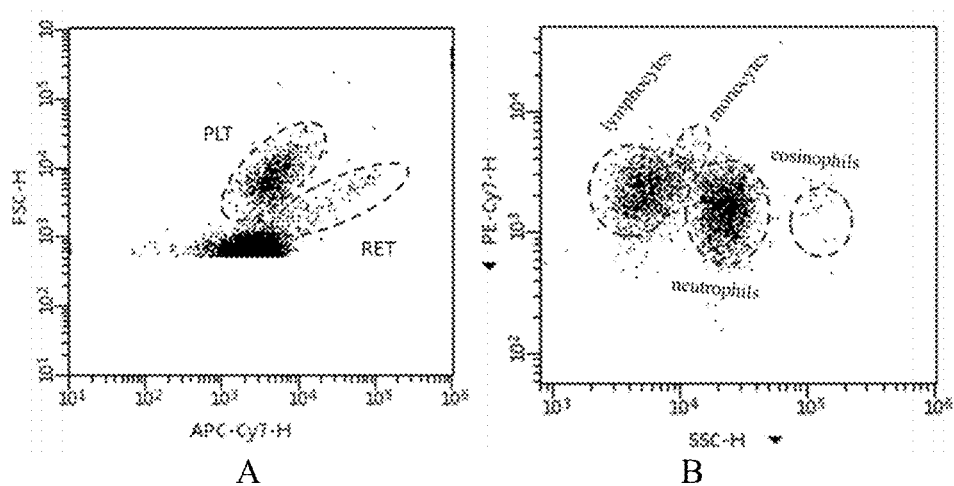
FIG. 14 illustrates a fluorescence-forward scattered light intensity scatter diagram (A) obtained by detecting platelets and reticulocytes by adding a nucleic acid dye under a deep hemolysis condition of Example 5, and a fluorescence-side scattered light intensity scatter diagram (B) of white blood cells.

20 μl of a fresh blood sample was added into 1 mL of the solution prepared according to the above-mentioned formula, incubation was performed at 45° C. for 60 seconds, and then detection was performed by adopting a flow cytometer (Mindray BriCyte E6). The excitation wavelength was set as 633 nm, the gain was set as 500, and 90° side fluorescence intensity information and 0° forward scattered light intensity information were collected to obtain a two-dimensional cell scatter diagram, as shown in FIG. 14A.

As shown in the figure, RET and PLT can be clearly differentiated by fluorescence signals and forward scattered light signals, respectively. By the ratios of the divided PLT and RET scatter dots in combination with the injection volume of the flow cytometer, the PLT concentration of this sample can be calculated to be 189×109/L, and the RET concentration can be calculated to be 101×109/L. The numerical value of PLT detected by adopting a traditional manual microscopic examination was 201×109/L, and the concentration of RET was 112×109/L. It is proved that PLT and RET in the blood sample can be effectively differentiated and counted by the method of the present disclosure.

The same treatment was performed on another 20 μl of the same blood sample, and measurement was performed in the same flow cytometer. The excitation wavelength was set as 633 nm, the gain was set as 100,000, and 90° side fluorescence intensity information and 90° side scattered light intensity information were collected to obtain a two-dimensional cell scatter diagram, as shown in FIG. 14B.

White blood cells can be clearly divided into four types, including lymphocytes, monocytes, neutrophils plus basophils, and eosinophils. The WBC concentration of this sample can be calculated to be 6.54×109/L according to the ratio of the divided WBC scatter dots in combination with the injection volume of the flow cytometer. The WBC concentration of the same sample measured by using a traditional reference method combined with a Beckman particle counter Z2 was 6.32×109/L. It can be seen that the two methods have a relatively good consistency therebetween.

The ratios obtained by dividing lymphocytes, monocytes, neutrophils plus basophils, and eosinophils were 19.8%, 3.2%, 75.8%, and 1.2%, respectively. After this sample was tested on the Mindray blood cell analyzer 6800, the obtained ratios of lymphocytes, monocytes, neutrophils plus basophils, and eosinophils were 20.3%, 2.9%, 75.1%, and 1.7%, respectively. And the above-mentioned results show that the white blood cell division performed by the method of the present disclosure has a relatively good correlation with the ratios obtained by the commercially available blood cell analyzer.

Example 6 Deeply Hemolyzing and Adding a Nucleic Acid Dye to Detect Platelets and White Blood Cells by Light Scattering and Fluorescence Signals A detection reagent of the present disclosure was prepared according to the following formula.

| | |
|---|---|
| Fluorescent Dye Alexa Fluor 488 | 0.8 ppm |
| Alkyl Glycoside (APG0814) | 0.6 g/L |
| TRIS | 40 Mm |
| Sodium Citrate | 5 g/L |
| Polyoxyethylene (23) Cetyl Ether | 0.5 g/L |
| PH | 7.5 |

Figure 15:
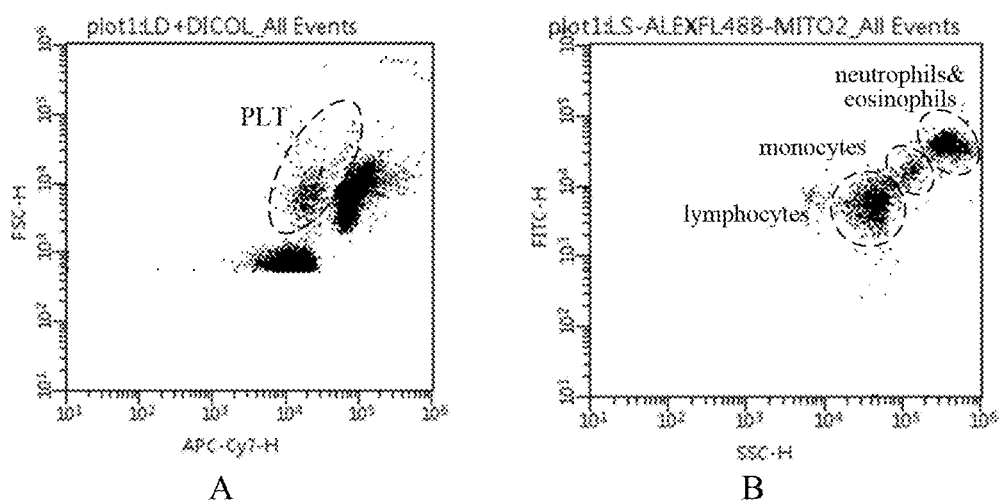
FIG. 15 illustrates a fluorescence-forward scattered light intensity scatter diagram (A) obtained by detecting platelets and reticulocytes by adding a membrane dye under a deep hemolysis condition of Example 6, and a fluorescence-side scattered light intensity scatter diagram (B) of white blood cells.

20 μl of a fresh blood sample was added to 1 mL of the solution prepared according to the above-mentioned formula, incubation was performed at 45° C. for 60 seconds, and then detection was performed by adopting a flow cytometer (Mindray BriCyte E6). The excitation wavelength was set as 488 nm, the gain was set as 500, 90° side fluorescence intensity information and 0° forward scattered light intensity information were collected to obtain a two-dimensional cell scatter diagram, as shown in FIG. 15.

From FIG. 15A, it can be seen that the two dark particle clusters (at the lower part and the right side) both consist of lysed red blood cell fragments, and the middle particle cluster consists of platelets, which indicates that the platelets can also be clearly differentiated from the red blood cell fragments by this method.

The same treatment was performed on another 20 μl of the same blood sample, and measurement was performed in the same flow cytometer. The excitation wavelength was set as 633 nm, the gain was set as 100,000, and 90° side fluorescence intensity information and 90° side scattered light intensity information were collected to obtain a cell scatter diagram.

As shown in FIG. 15B, the ratios obtained by dividing lymphocytes, monocytes, and neutrophils plus eosinophils were 16.4%, 6.1%, and 77.5%, respectively; while after this sample was tested on the Mindray blood cell analyzer 6800, the ratios of lymphocytes, monocytes, neutrophils and eosinophils were 16%, 5.8%, 78.2 and 1.9%, respectively. The above-mentioned results show that the white blood cell division performed by the method of the present disclosure has a relatively good correlation with the ratios obtained by the commercially available blood cell analyzer.

Example 7 Deeply Hemolyzing and Adding a Mitochondrion Dye to Detect Platelets and White Blood Cells by Light Scattering and Fluorescence Signals A detection reagent of the present disclosure was prepared according to the following formula:

| Fluorescence Dye Mitotracker Red | 0.8 ppm |
| --- | --- |
| Alkyl Glycoside (APG0814) | 0.6 g/L |
| TRIS | 40 Mm |
| Sodium Citrate | 5 g/L |
| Polyoxyethylene (23) Cetyl Ether | 0.5 g/L |
| PH | 7.5 |

20 μl of a fresh blood sample was added into 1 mL of the solution prepared according to the above-mentioned formula, incubation was performed at 45° C. for 60 seconds, and then detection was performed using a flow cytometer (Mindray BriCyte E6). The excitation wavelength was set as 633 nm, the gain was set as 500, and 90° side fluorescence intensity information and 90° side scattered light intensity information were collected to obtain a two-dimensional cell scatter diagram, as shown in FIG. 16.

Figure 16:
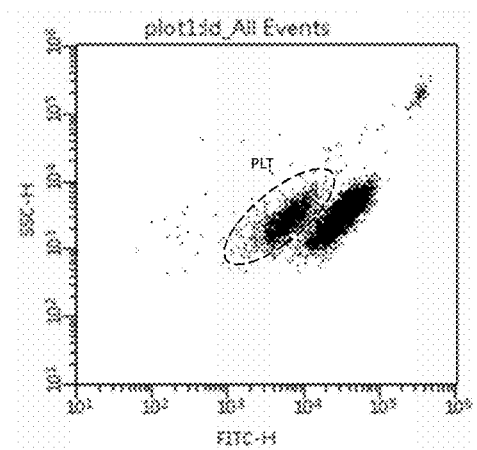
FIG. 16 illustrates a fluorescence-side scattered light intensity scatter diagram obtained by detecting platelets and reticulocytes by adding a mitochondrion dye under a deep hemolysis condition of Example 7.

Two particle clusters can be seen in FIG. 16, wherein the particle cluster at the right side consists of lysed red blood cell fragments, and the particle cluster at the left side consists of platelets, which indicates that the platelets can also be clearly differentiated from the red blood cell fragments by this method.

Example 8 Deeply Hemolyzing and Adding a Membrane Dye and a Nucleic Acid Dye to Detect Platelets and Reticulocytes by Light Scattering and Fluorescence Signals A detection reagent of the present prevention was prepared according to the following formula:

| Membrane Fluorescence Dye Alexa Fluor 488 | 0.8 ppm |
| --- | --- |
| Nucleic Acid Dye SYTO9 | 0.6 ppm |
| Alkyl Glycoside (APG0814) | 0.6 g/L |
| TRIS | 40 Mm |
| Sodium Citrate | 5 g/L |
| Polyoxyethylene (23) Cetyl Ether | 0.5 g/L |
| PH | 7.5 |

Figure 17:
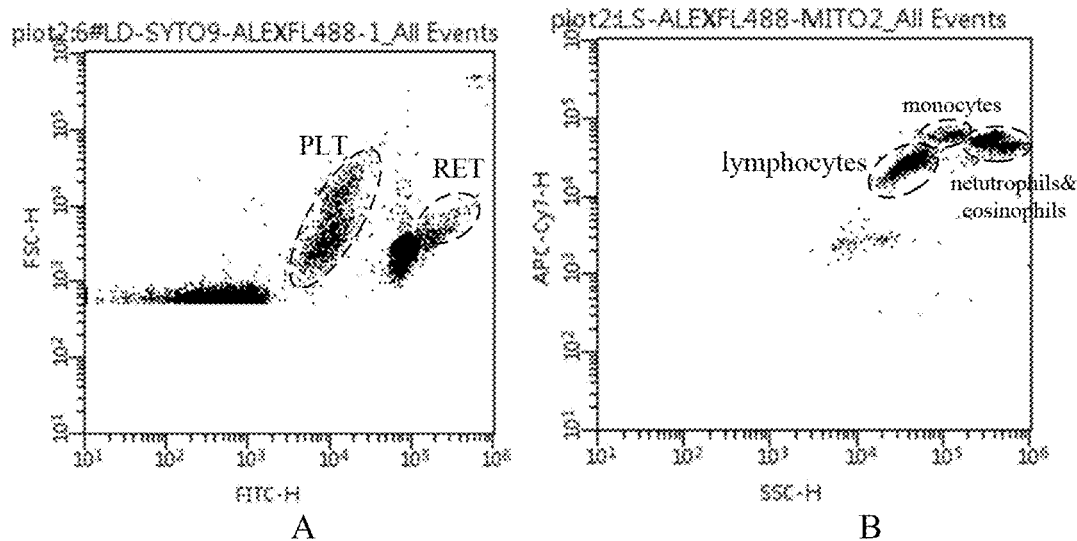
FIG. 17 illustrates a fluorescence-forward scattered light intensity scatter diagram (A) obtained by detecting platelets and reticulocytes by adding a membrane dye and a nucleic acid dye under a deep hemolysis condition of Example 8, and a fluorescence-side scattered light intensity scatter diagram (B) of white blood cells.

20 μl of a fresh blood sample was added into 1 mL of the solution prepared according to the above-mentioned formula, incubation was performed at 45° C. for 60 seconds, and then detection was performed by adopting a flow cytometer (Mindray BriCyte E6). The excitation wavelength was set as 488 nm, the gain was set as 500, and 90° side fluorescence intensity information and 0° forward scattered light intensity information were collected to obtain a two-dimensional cell scatter diagram, as shown in FIG. 17.

As shown in FIG. 17A, the two dark particle clusters both consist of lysed red blood cell fragments, and the middle particle cluster consists of platelets, which indicates that the platelets can be more significantly differentiated from the red blood cell fragments by this method. The particle cluster at the rightmost side is identified as reticulocytes, therefore information of reticulocytes can be further obtained by this method.

The same treatment was performed on another 20 μl of the same blood sample, and measurement was performed in the same flow cytometer. The excitation wavelength was set as 633 nm, the gain was set as 100,000; and 90° side fluorescence intensity information and 90° side scattered light intensity information were collected to obtain a cell scatter diagram.

As shown in FIG. 17B, the ratios obtained by dividing lymphocytes, monocytes, and neutrophils plus eosinophils were 16.8%, 6.4%, and 76.8%, respectively; while after this sample was tested on the Mindray blood cell analyzer 6800, the ratios of lymphocytes, monocytes, neutrophils and eosinophils were 16%, 5.8%, 78.2 and 1.9%, respectively. The above-mentioned results show that the white blood cell division performed by the method of the present disclosure has a relatively good correlation with the ratios obtained by the commercially available blood cell analyzer.

Example 9 Correlation of Testing PLT and RET

A detection reagent of the present prevention was prepared according to the following formula:

| Fluorescence Dye (structural formula is shown as follows) | 1.0 ppm |
| --- | --- |
| Decyl Glucoside | 0.6 g/L |
| TRIS | 40 Mm |
| Sodium Citrate | 5 g/L |
| Polyoxyethylene (23) Cetyl Ether | 0.5 g/L |
| PH | 7.5 |

Structural Formula of Fluorescence Dye:

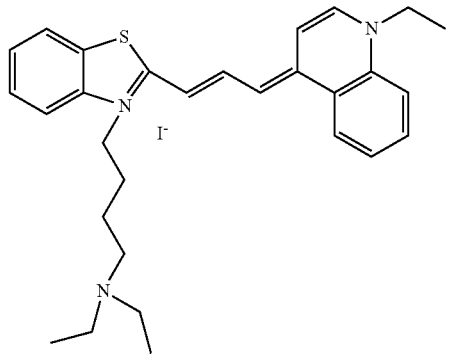 [SMILES: CCN(CC)CCCC[n+]1c(/C=C/C=C2\C=CN(CC)c3ccccc32)sc2ccccc21 ; [I-]]

Figure 18:
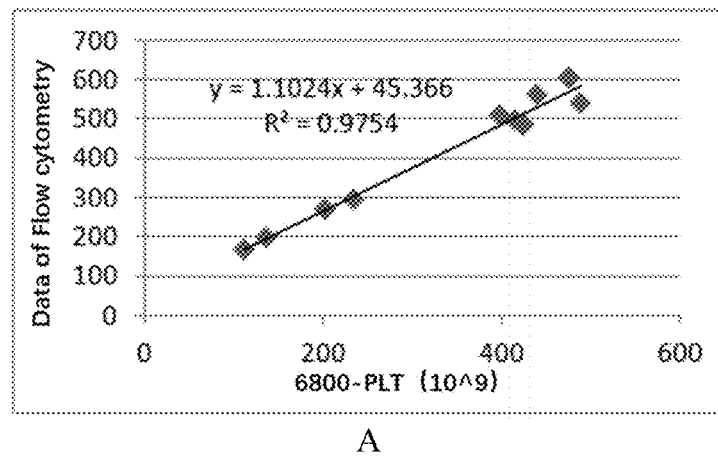
FIG. 18 illustrates a diagram related to test of platelets (A) and reticulocytes (B) in Example 9.
Figure 18:
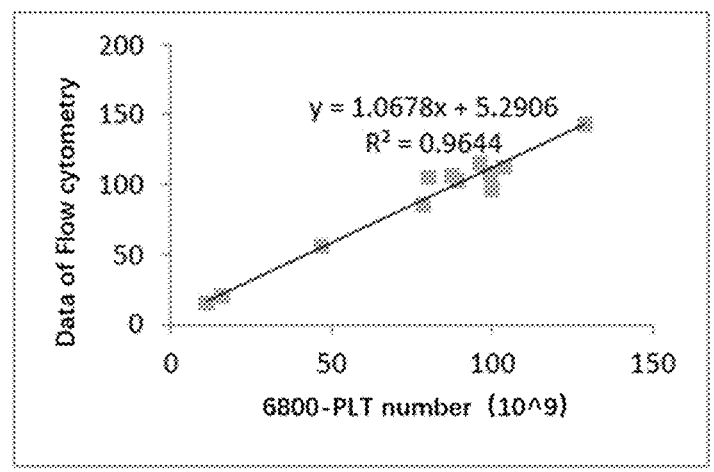

12 fresh blood samples were selected, 20 μl of each sample was added into 1 mL of the above-mentioned solution, and after incubation was performed at 45° C. for 60 seconds, data was collected using a flow cytometer (Mindray BriCyte E6, the excitation wavelength was 633 nm, and the gain was set as 500). 90° side fluorescence intensity information and 0° forward scattered light intensity information were collected. RET and PLT can be differentiated by fluorescence signals and forward scattered light signals, respectively. The PLT concentration and the RET concentration of the corresponding sample can be calculated according to the ratios of the divided PLT and RET scatter dots and the injection volume of the flow cytometer. Subsequently, the same 12 samples were tested using the Mindray blood cell analyzer 6800, and the PLT concentration and the RET concentration provided by the analyzer were recorded. According to the detection data, for PLT concentration and RET concentration, diagrams showing the correlation between the detection results obtained on the flow cytometer by adopting the method of the present disclosure and the detection results obtained on the Mindray blood cell analyzer 6800 by adopting a conventional method are drawn, respectively, as shown in FIG. 18A and FIG. 18B.

As seen from the figures, compared with the test results of the Mindray blood cell analyzer 6800, PLT and RET can be differently stained by a nucleic acid dye in a deep hemolysis condition, and related particles can be counted. The test results of the two methods have a quite good correlation therebetween.

Example 10 Analysis of Blood Sample by Using Fluorescence Dye Alexa Fluor 488

Reagent Preparation:

First Reagent

| Dodecyl Trimethyl Ammonium Chloride | 550 mg |
| --- | --- |
| Brij35 | 1.5 g |
| Trishydroxymethyl aminomethane | 13 g |
| Pure Water | 1 L |
| pH | 7.0 |

Second Reagent

| Dye Alexa Fluor 488 | 30 mg |
| --- | --- |
| Glycol | 950 ml |
| Methanol | 50 ml |

Figure 19:
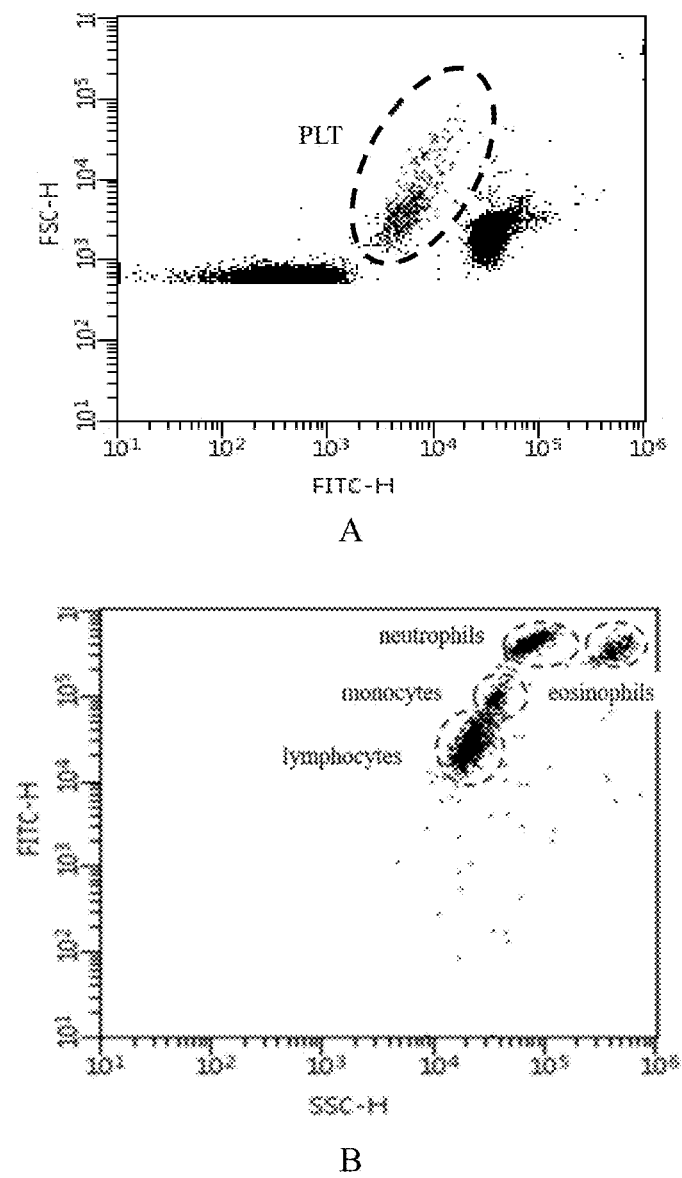
FIG. 19 illustrates the staining and differentiation effects of Alexa Fluor 488 on platelets (A) and white blood cells (B) under a hemolysis condition of Example 10.

20 μl of a fresh blood was added into 1 mL of the above-mentioned first reagent solution, and 20 μl of the second reagent was added. After incubation was performed at 35° C. for 60 seconds, data was collected (the excitation wavelength was 488 nm) using a flow cytometry (Mindray BriCyte E6), the gain was set as 500, 90-degree side fluorescence signals were collected as fluorescence staining information, and forward scattered light intensity information with a measurement angle of 0 degree was also adopted. A cell scatter diagram is shown in FIG. 19.

As seen from FIG. 19A, when the membrane dye Alexa Fluor 488 is used, platelets (in the circle) can be effectively differentiated from blood ghost, and white blood cells can also be stained well by the dye and thus can be classified and counted. The platelet count of the sample was calculated to be 216×109/L through the injection volume and the test particle number of platelets, and the measurement value obtained by using a counting method of classic manual microscopic examination was also 216×109/L.

According to FIG. 19B, white blood cells were counted by using the same method, and the obtained result was 8.86×109/L, while the numerical value measured by the Beckman particle counter Z2 was 8.81×109/L, and the two results have a relatively good consistency therebetween. The ratios obtained by dividing lymphocytes, monocytes, neutrophils and eosinophils were 17.8%, 4.8%, 75.8% and 1.6%, respectively; while after this sample was tested in the Mindray blood cell analyzer 6800, the ratios of lymphocytes, monocytes, neutrophils plus basophils, and eosinophils were 18.1%, 5.1%, 74.8% and 2.0%, respectively. The above-mentioned results show that the white blood cell division performed by the method has a relatively good correlation with the ratios obtained by the blood cell analyzer.

Example 11 Analysis of Blood Sample by Using Dye DiD

Reagent Preparation:

First Reagent

| Tetradecyl Trimethyl Ammonium Chloride | 550 mg |
| --- | --- |
| Brij35 | 1.5 g |
| Trishydroxymethyl aminomethane | 13 g |
| Pure Water | 1 L |
| pH | 7.0 |

Second Reagent

| Dye DiD | 30 mg |
| --- | --- |
| Glycol | 950 ml |
| Methanol | 50 ml |

Figure 20:
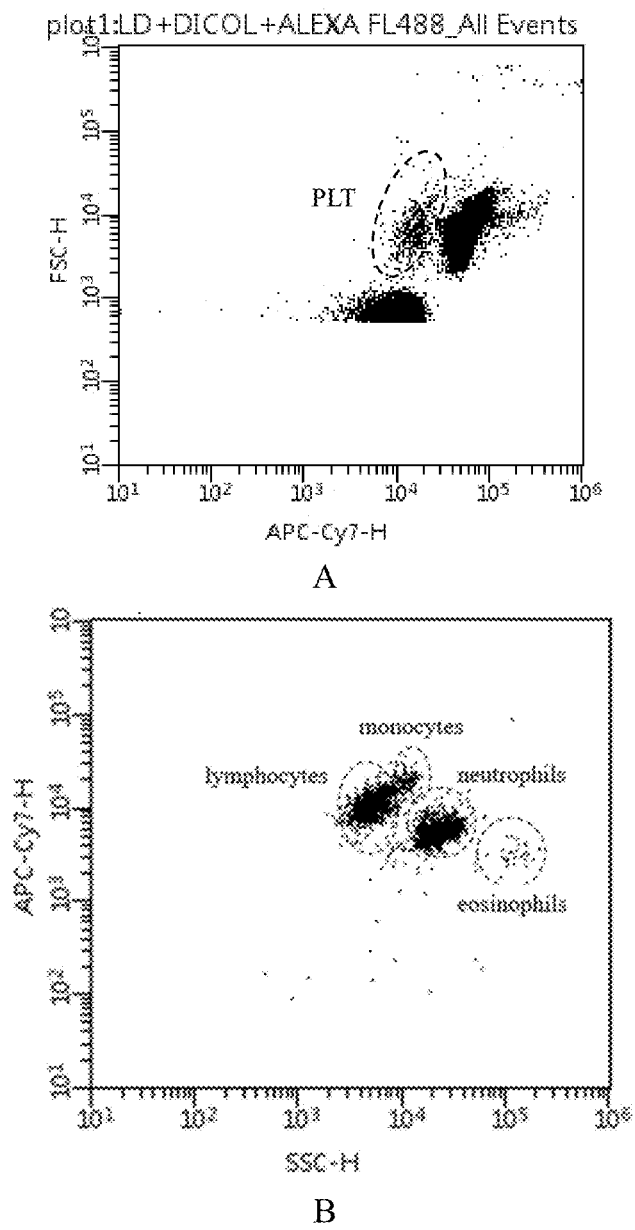
FIG. 20 illustrates the staining and differentiation effects of DiD on platelets (A) and white blood cells (B) under a hemolysis condition of Example 11.

20 μl of a fresh blood was added into 1 mL of the above-mentioned first reagent solution, and 20 μl of the second reagent was added. After incubation was performed at 35° C. for 60 seconds, data was collected (the excitation wavelength was 633 nm) using a flow cytometry (Mindray BriCyte E6), the gain was set as 500, 90-degree side fluorescence signals were collected as fluorescence staining information, and forward scattered light intensity information with a measurement angle of 0 degree was also adopted. A cell scatter diagram is shown in FIG. 20.

It can be seen from FIG. 20A that after being stained by the dye, platelets can be effectively differentiated from blood ghost. By dividing the scatter dots of the platelets, the concentration of platelets was calculated to be 158×109/L; while the measurement value obtained by using a counting method of classic manual microscopic examination was 160×109/L. Therefore, platelet particles can be effectively differentiated and counted by using the dye in a hemolysis condition.

According to FIG. 20B, white blood cells were counted by using the same method, and the obtained result was 4.35×109/L, while the measurement value obtained by adopting a reference method in combination with the Beckman particle counter Z2 was 4.28×109/L. The two results have a relatively good consistency therebetween. The ratios obtained by dividing lymphocytes, monocytes, neutrophils and eosinophils were 14.8%, 6.8%, 74.5% and 3.9%, respectively; while after this sample was tested in the Mindray blood cell analyzer 6800, the ratios of lymphocytes, monocytes, neutrophils and eosinophils were 15.9%, 7.2%, 72.2% and 4.7%, respectively. The above-mentioned results show that the white blood cell division performed by the method of the present disclosure has a relatively good correlation with the ratios obtained by the blood cell analyzer.

Example 12 Analysis of Blood Sample by Using Dye Rhodamine 123

Reagent Preparation:

First Reagent

| Dodecyl Trimethyl Ammonium Chloride | 550 mg |
| --- | --- |
| Brij35 | 1.5 g |
| Trishydroxymethyl aminomethane | 13 g |
| Pure Water | 1 L |
| pH | 7.0 |

Second Reagent

| | |
|---|---|
| Dye Rhodamine 123 | 30 mg |
| Glycol | 950 ml |
| Methanol | 50 ml |

20 µl of a fresh blood was added into 1 mL of the above-mentioned first reagent solution, and 20 µl of the second reagent was added. After incubation was performed at 35° C. for 60 seconds, data was collected (the excitation wavelength was 488 nm) using a flow cytometer (Mindray BriCyte E6), the gain was set as 500, and 90-degree side fluorescence signals were collected as fluorescence staining information, and forward scattered light intensity information with a measurement angle of 0 degree was also adopted. A cell scatter diagram is shown in FIG. 21A.

Figure 21:
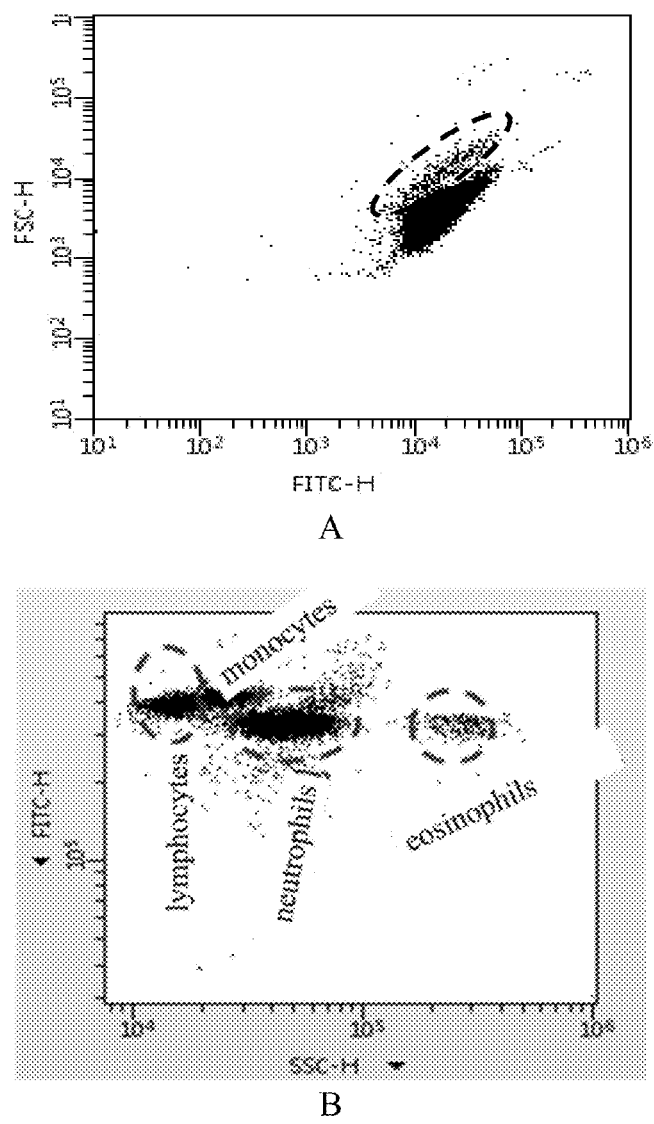
FIG. 21 illustrates the staining and differentiation effects of Rhodamine 123 on platelets (A) and white blood cells (B) under a hemolysis condition of Example 12.

It can be seen from FIG. 21A that after being stained by the dye Rhodamine 123, platelets can be effectively differentiated from blood ghost. By dividing the scatter dots of platelets, the concentration of platelets was calculated to be 208×109/L; while the measurement value obtained by using a counting method of manual microscopic examination was 201×109/L. Therefore, platelet particles can be effectively differentiated and counted by using the dye Rhodamine 123 in a hemolysis condition.

According to FIG. 21B, white blood cells were counted by using the same method, and the obtained result was 4.02×109/L, while the numerical value measured by adopting a reference method in combination with the Beckman particle counter Z2 was 3.98×109/L. The two results have a relatively good consistency therebetween. The ratios obtained by dividing lymphocytes, monocytes, neutrophils and eosinophils were 15.9%, 7.1%, 71.5% and 5.5%, respectively; while after this sample was tested in the Mindray blood cell analyzer 6800, the ratios of lymphocytes, monocytes, neutrophils and eosinophils were 15.9%, 6.8%, 72.2% and 5.1%, respectively. The above-mentioned results show that the white blood cell division performed by the method of the present disclosure has a relatively good correlation with the ratios obtained by the blood cell analyzer.

Example 13 Analysis of Blood Sample by Using Dye Mitotracker Deep Red

Reagent Preparation:
First Reagent

| | |
|---|---|
| Tetradecyl Trimethyl Ammonium Chloride | 550 mg |
| Triton 100 | 0.75 g |
| Trishydroxymethyl aminomethane | 13 g |
| Pure Water | 1 L |
| pH | 7.0 |

Second Reagent

| | |
|---|---|
| Dye Mitotracker Deep Red | 30 mg |
| Glycol | 950 ml |
| Methanol | 50 ml |

Figure 22:
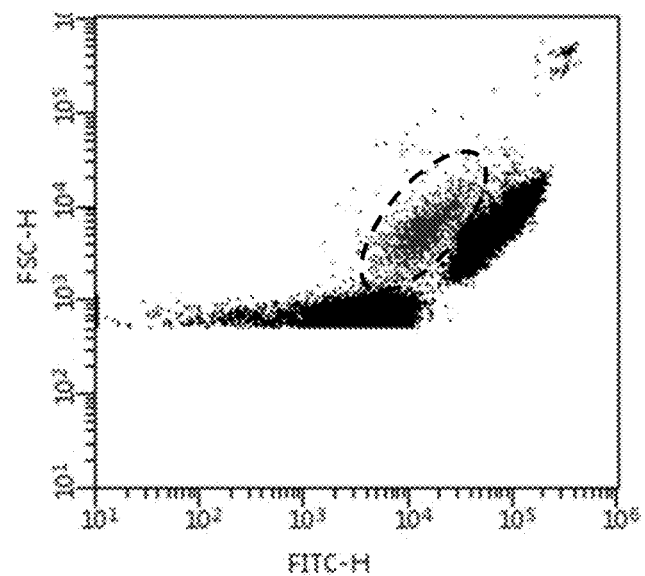
FIG. 22 illustrates the staining and differentiation effects of Mitotracker Deep Red on platelets (A) and white blood cells (B) under a hemolysis condition of Example 13.
Figure 22:
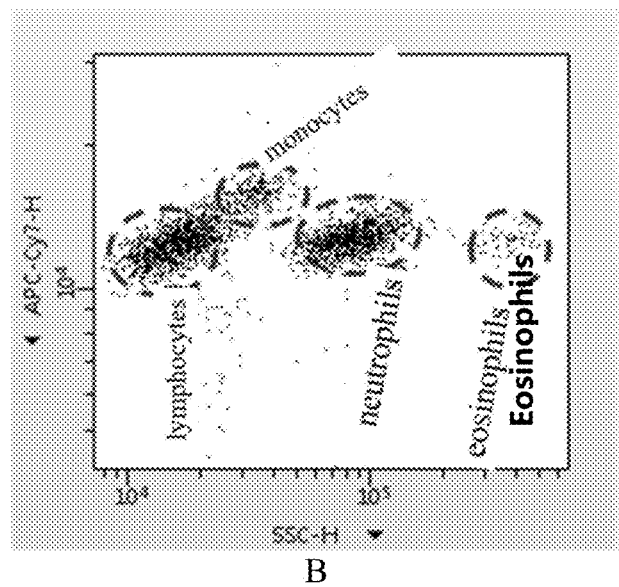

20 µl of a fresh blood was added to 1 mL of the above-mentioned first reagent solution, and 20 µl of the second reagent was added. After incubation was performed at 35° C. for 60 seconds, data was collected (the excitation wavelength was 633 nm) using a flow cytometer (Mindray BriCyte E6), the gain was set as 500, and 90-degree side fluorescence signals were collected as fluorescence staining information, and forward scattered light intensity information with a measurement angle of 0 degree was also adopted. A cell scatter diagram is shown in FIG. 22.

It can be seen from FIG. 22A that, when Mitotracker Deep Red was used, platelets (in a range represented by dotted line in the figure) can be differentiated from blood ghost, wherein light-color scatter dots represent platelets, and by dividing the scatter dots of the platelets, the concentration of PLT was calculated to be 165×109/L; while the concentration of PLT obtained by using a counting method of classic manual microscopic examination was 201×109/L. It can be seen that platelets can also be differentiated by using the Dye Mitotracker Deep Red.

According to FIG. 22B, white blood cells were counted by using the same method, and the obtained result was 5.12×109/L, while the measurement value obtained by adopting a reference method in combination with the Beckman particle counter Z2 was 5.08×109/L. The two results have a relatively good consistency therebetween. The ratios obtained by dividing lymphocytes, monocytes, neutrophils and eosinophils were 14.8%, 7.8%, 74.5% and 2.9%, respectively; while after this sample was tested in the Mindray blood cell analyzer 6800, the ratios of lymphocytes, monocytes, neutrophils and eosinophils were 15.9%, 7.2%, 73.2% and 3.7%, respectively. The above-mentioned results show that the white blood cell division performed by the method of the present disclosure has a relatively good correlation with the ratios obtained by the blood cell analyzer.

Example 14 Analysis of Blood Sample by Using Dye Mitotracker Red

Reagent Preparation:
First Reagent

| | |
|---|---|
| Dodecyl Trimethyl Ammonium Chloride | 550 mg |
| Tween 20 | 1.0 g |
| Trishydroxymethyl aminomethane | 13 g |
| Pure Water | 1 L |
| pH | 7.0 |

Second Reagent

| | |
|---|---|
| Dye Mitotracker Red | 30 mg |
| Glycol | 950 ml |
| Methanol | 50 ml |

Figure 23:
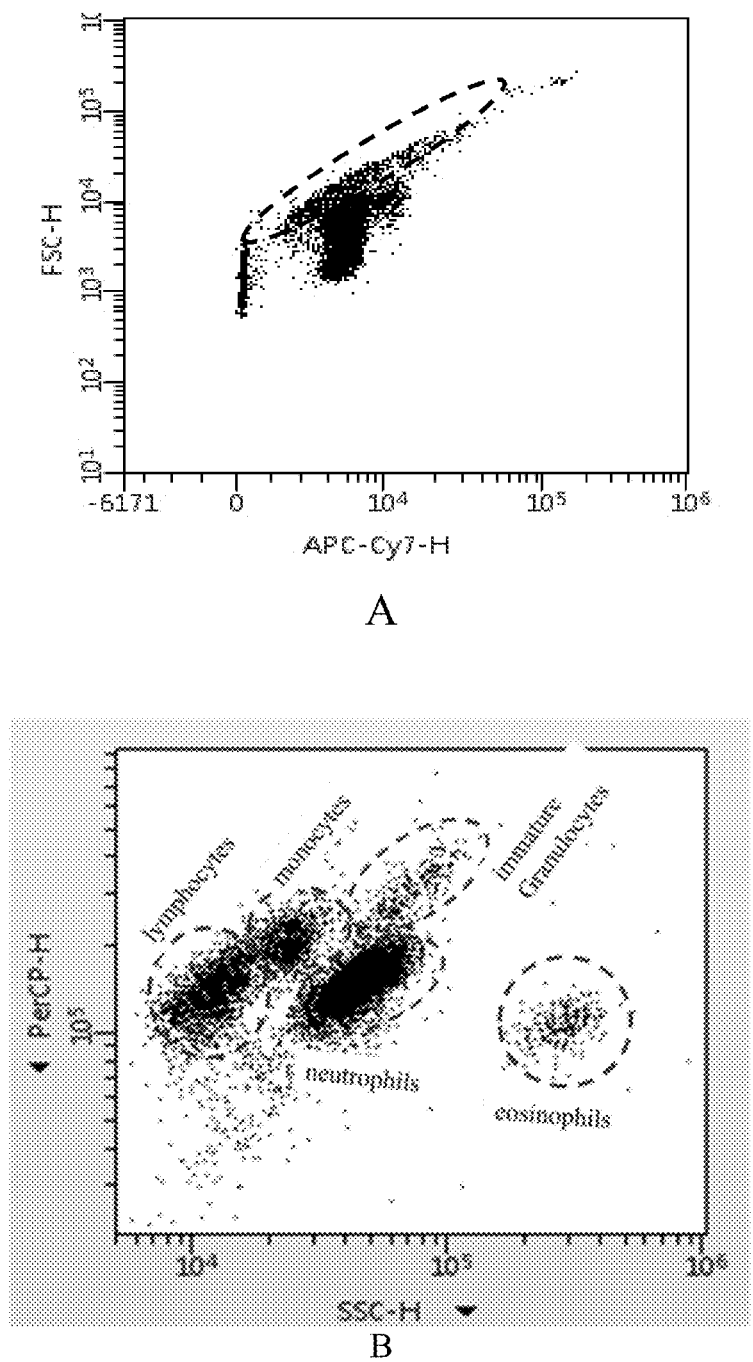
FIG. 23 illustrates the staining and differentiation effects of Mitotracker Red on platelets (A) and white blood cells (B) under a hemolysis condition of Example 14.

20 µl of a fresh blood was added to 1 mL of the above-mentioned first reagent solution, and 20 µl of the second reagent was added. After incubation was performed at 35° C. for 60 seconds, data was collected (the excitation wavelength was 488 nm) using a flow cytometer (Mindray BriCyte E6), the gain was set as 500, and 90-degree side fluorescence signals were collected as fluorescence staining information, and forward scattered light intensity information with a measurement angle of 0 degree was also adopted. A cell scatter diagram is shown in FIG. 23.

It can be seen from FIG. 23A that when the dye Mitotracker Red was used, platelets (in a range represented by dotted line in the figure) can be effectively differentiated from blood ghost, and meanwhile it can be seen from FIG. 23B that white blood cells can also be effectively classified based on the staining performance of the dye on white blood cells, thereby achieving effective classification and counting of platelets while detecting white blood cells. Through the injection volume and the test particle number of platelets, the platelet count of the sample was calculated to be 176×109/L, while the measurement value obtained by using a counting method of classic manual microscopic examination was 172×109/L The two results have a relatively good consistency therebetween.

According to FIG. 23B, white blood cells were counted by using the same method, and the obtained result was 7.65×109/L, while the measurement value obtained by adopting a reference method in combination with the Beckman particle counter Z2 was 7.73×109/L. The two results have a relatively good consistency therebetween. The ratios obtained by dividing lymphocytes, monocytes, neutrophils eosinophils, and immature granulocytes were 13.7%, 6.1%, 77.5%, 0.7% and 2.0%, respectively; while after this sample was tested in the Mindray blood cell analyzer 6800, the ratios of lymphocytes, monocytes, neutrophils eosinophils, and immature granulocytes were 14.1%, 5.8%, 76.2%, 1.9% and 2.0%, respectively. The above-mentioned results show that the white blood cell division performed by the method has a relatively good correlation with the ratios obtained by the blood cell analyzer.

Example 15 Verification of Correlation of Platelet Test by Taking Example 10 as Example Reagent Preparation: same as Example 10

20 fresh blood samples were provided, and the testing method for each blood sample comprised the steps as follows: adding 20 μl of a fresh blood into 1 mL of the above-mentioned prepared first reagent solution and also adding 20 μl of the second reagent; after performing incubation at 35° C. for 60 seconds, collecting data (the excitation wavelength was 488 nm) by using a flow cytometer (Mindray BriCyte E6); setting the gain as 500; collecting 90-degree side fluorescence signals as fluorescence staining information; and adopting forward scattered light intensity information with a measurement angle of 0 degree. The platelet concentration of the blood sample was calculated by dividing the scatter dots of platelets in combination with the injection volume in the flow cytometer. After the test was ended, the blood samples were tested in a Mindray 6800 instrument, and test values of platelets were recorded. A correlation curve is drawn by using the results obtained by the two testing methods.

Figure 24:
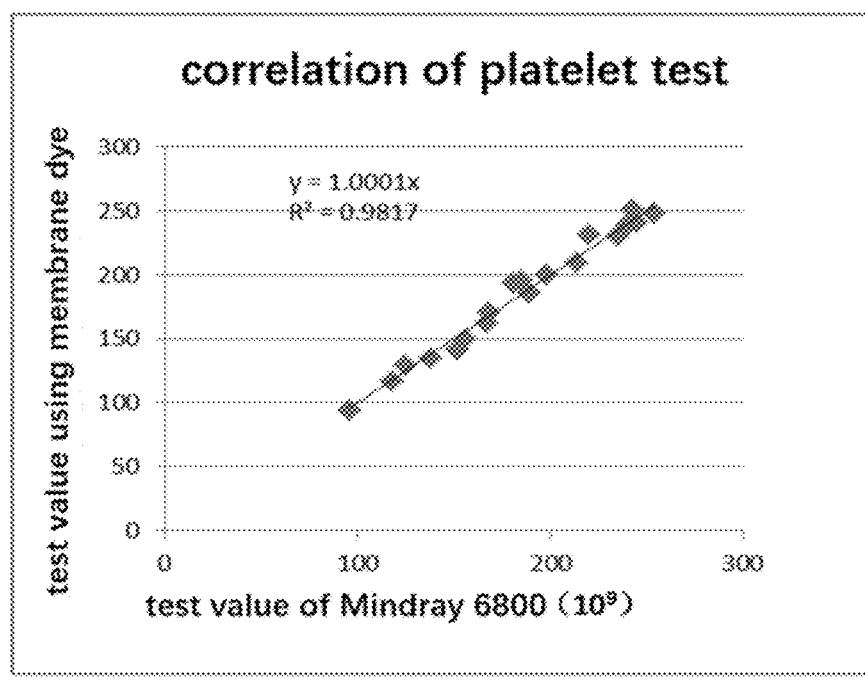
FIG. 24 illustrates the correlation between a staining method of Example 15 and a Mindray 6800 instrument in terms of testing values.

It can be seen from FIG. 24 that when the membrane dye Alexa Fluor 488 is used to test platelets, its test values have a relatively good consistency with the test values of the Mindray 6800 instrument, and the correlation coefficient was 0.9817 within a numerical range from 100×109/L to 250×109/L.

The contents described above are only some embodiments of the present disclosure but are not meant to limit the patent scope of the present disclosure. Any equivalent structural modifications based on the description and drawings of the present disclosure, or direct/indirect applications in other related technical fields under the inventive concept of the present disclosure are all included in the patent protection scope of the present disclosure.

The invention claimed is:

1. A blood detection method, comprising:
    treating a blood sample with a first reagent to obtain a test sample, the first reagent comprising a hemolytic agent for lysing red blood cells in the blood sample into fragments having light scattering characteristics significantly different from those of platelets;
    passing particles in the test sample through a detection area of an optical detection system one by one to obtain optical information of the test sample; and
    obtaining optical information of platelets according to at least two types of the optical information of the test sample.

2. The blood detection method of claim 1, wherein the at least two types of the optical information of the test sample comprise forward scattered light intensity and side scattered light intensity to differentiate platelets and lysed red blood cell fragments.

3. The blood detection method of claim 2, further comprising obtaining optical information of white blood cells according to the forward scattered light intensity and the side scattered light intensity to differentiate white blood cell subpopulations according to the obtained optical information of white blood cells, wherein the white blood cell subpopulations at least comprise monocytes, lymphocytes and neutrophils.

4. The blood detection method of claim 1, wherein the hemolytic agent comprises at least one selected from alkyl glycoside, triterpenoid saponin, and steroidal saponin.

5. The blood detection method of claim 4, wherein the alkyl glycoside is selected from glycoside compounds having the general formula I:

$$R-(CH_2)_n-CH_3 \tag{1}$$

wherein R is selected from the group consisting of monosaccharide, deoxy monosaccharide and polysaccharide, and n is an integer of 5-17.

6. The blood detection method of claim 1, wherein the first reagent further comprises:
    a nonionic surfactant having the general formula II:

$$R_1-R_2-(CH_2CH_2O)_m-H \tag{II}$$

wherein R1 is a C8-C23 alkyl group, R2 is —O—, or —COO—, and m is an integer of 10 to 50; and
    optionally, at least one organic acid or a salt thereof, wherein the organic acid or the salt thereof is selected from the group consisting of organic acids having at least one carboxyl group or sulfonic acid group and alkali metal salts thereof.

7. The blood detection method of claim 1, further comprising treating the blood sample with a second reagent, and the second reagent comprises a fluorescent dye.

8. The blood detection method of claim 7, wherein the optical information of the test sample comprises side scattered light intensity information and fluorescence intensity information, and white blood cell subpopulations are differentiated and/or immature granulocytes are identified according to the side scattered light intensity information and the fluorescence intensity information, wherein the white blood cell subpopulations at least comprise monocytes, lymphocytes and neutrophils.

9. The blood detection method of claim 7, wherein the fluorescence dye comprises a first fluorescence dye selected from a membrane-specific dye and a mitochondrion-specific dye.

10. The blood detection method of claim 9, wherein the membrane-specific dye is selected from the group consisting of DiA, DiD, DiI, DIO, DIR, DIS, FDA, Alexa Fluor 488, Super Fluor 488 and variant structures using them as parent, and the mitochondrion-specific dye is selected from the group consisting of Janus Green B, MitoLite Red, Rhodamine 123 and Mitotracker series as well as their parents.

11. The blood detection method of claim 9, wherein the optical information of the test sample comprises forward scattered light intensity information and fluorescence intensity information, and platelets are identified according to the fluorescence intensity information and the forward scattered light intensity information;

and/or the method further comprises providing an alarm for reticulocytes when a number of particles in a preset region of a scatter diagram generated according to the forward scattered light intensity and the fluorescence intensity exceeds a predetermined threshold value.

12. The blood detection method of claim 7, wherein the fluorescence dye comprises a second fluorescence dye selected from nucleic acid-specific dyes, and the nucleic acid-specific dyes are preferably nucleic acid-specific dyes for reticulocytes.

13. The blood detection method of claim 12, wherein the optical information of the test sample comprises scattered light intensity information and fluorescence intensity information, and the method further comprises identifying reticulocytes according to the fluorescence intensity information and the scattered light intensity information.

14. The blood detection method of claim 13, wherein the optical information of the test sample further comprises forward scattered light intensity information, and the method further comprises:

differentiating platelets and reticulocytes according to the fluorescence intensity information and the forward scattered light intensity information; and counting reticulocytes according to the fluorescence intensity information and the forward scattered light intensity information.

15. The blood detection method of claim 7, wherein the fluorescence dye comprises a first fluorescence dye selected from a membrane-specific dye and a mitochondrion-specific dye, and a second fluorescence dye selected from nucleic acid-specific dyes.

16. The blood detection method of claim 15, wherein the optical information of the test sample comprises side scattered light intensity information and fluorescence intensity information, and the method further comprises differentiating platelets and reticulocytes according to the fluorescence intensity information and the side scattered light intensity information.

17. The blood detection method of any one of claim 1, further comprising counting platelets according to the obtained optical information of platelets.

* * * * *